US008426675B2

(12) United States Patent
Dickins et al.

(10) Patent No.: US 8,426,675 B2
(45) Date of Patent: Apr. 23, 2013

(54) METHODS FOR PRODUCING MICRORNAS

(75) Inventors: Ross Dickins, Carlton (AU); Scott W. Lowe, Cold Spring Harbor, NY (US); Gregory J. Hannon, Huntington, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 13/155,087

(22) Filed: Jun. 7, 2011

(65) Prior Publication Data
US 2012/0084872 A1 Apr. 5, 2012

Related U.S. Application Data

(60) Division of application No. 12/156,957, filed on Jun. 5, 2008, now Pat. No. 7,993,925, which is a continuation of application No. 11/444,107, filed on May 31, 2006, now abandoned.

(60) Provisional application No. 60/686,135, filed on May 31, 2005.

(51) Int. Cl.
*A01K 67/00* (2006.01)
*C07H 21/04* (2006.01)

(52) U.S. Cl.
USPC ........... 800/14; 536/24.1; 536/24.5; 536/23.2

(58) Field of Classification Search ................. None
See application file for complete search history.

(56) References Cited

U.S. PATENT DOCUMENTS

| | | | |
|---|---|---|---|
| 5,530,101 A | 6/1996 | Queen et al. |
| 5,593,676 A | 1/1997 | Bhat et al. |
| 5,672,485 A | 9/1997 | Foster et al. |
| 5,686,072 A | 11/1997 | Uhr et al. |
| 5,928,638 A | 7/1999 | Uchida et al. |
| 6,111,093 A | 8/2000 | Seed et al. |
| 6,134,982 A | 10/2000 | Takabatake et al. |
| 6,165,737 A | 12/2000 | Wang et al. |
| 6,306,393 B1 | 10/2001 | Goldenberg |
| 6,583,333 B1 | 6/2003 | Lowe et al. |
| 2002/0041847 A1 | 4/2002 | Goldenberg |
| 2002/0086356 A1 | 7/2002 | Tuschl et al. |
| 2002/0132346 A1 | 9/2002 | Cibelli |
| 2002/0155604 A1 | 10/2002 | Ledbetter et al. |
| 2003/0148409 A1 | 8/2003 | Rossi et al. |
| 2003/0226159 A1 | 12/2003 | Bachoo et al. |
| 2004/0006035 A1 | 1/2004 | Macejak et al. |
| 2004/0039010 A1 | 2/2004 | Grupp et al. |
| 2004/0045043 A1 | 3/2004 | Finney et al. |
| 2004/0053411 A1 | 3/2004 | Cullen et al. |
| 2004/0053869 A1 | 3/2004 | Andrews et al. |
| 2004/0202658 A1 | 10/2004 | Benyunes |
| 2005/0003541 A1 | 1/2005 | Katsuki et al. |
| 2005/0070693 A1 | 3/2005 | Hansen et al. |
| 2005/0075492 A1 | 4/2005 | Chen et al. |
| 2005/0143448 A1 | 6/2005 | Grenard et al. |
| 2005/0191302 A1 | 9/2005 | Arthur et al. |
| 2005/0233391 A1 | 10/2005 | Spies et al. |
| 2006/0040391 A1 | 2/2006 | Bailey et al. |
| 2006/0123494 A1 | 6/2006 | Wu et al. |
| 2006/0135456 A1 | 6/2006 | Hannon et al. |
| 2006/0162000 A1 | 7/2006 | Zender et al. |
| 2006/0240556 A1 | 10/2006 | Cibelli |
| 2006/0247193 A1 | 11/2006 | Taira et al. |
| 2006/0286584 A1 | 12/2006 | Duojia |
| 2006/0294604 A1 | 12/2006 | Fridman et al. |
| 2007/0033663 A1 | 2/2007 | Katsuki et al. |
| 2007/0044164 A1 | 2/2007 | Dickins et al. |
| 2007/0078084 A1 | 4/2007 | Kishore et al. |
| 2007/0178106 A1 | 8/2007 | Romagne |
| 2008/0025958 A1 | 1/2008 | Hannon et al. |
| 2008/0226553 A1 | 9/2008 | Lowe et al. |
| 2008/0242622 A1 | 10/2008 | Lowe et al. |
| 2009/0022685 A1 | 1/2009 | Lowe et al. |
| 2009/0029872 A1 | 1/2009 | Zender et al. |
| 2009/0082298 A1 | 3/2009 | Dickins et al. |
| 2009/0186839 A1 | 7/2009 | Lowe et al. |
| 2010/0273660 A1 | 10/2010 | Zender et al. |

FOREIGN PATENT DOCUMENTS

| | | |
|---|---|---|
| EP | 1092783 | 4/2001 |
| EP | 1247865 | 6/2005 |
| WO | WO-91/13974 | 9/1991 |
| WO | WO-94/09363 | 4/1994 |
| WO | WO-95/03770 | 2/1995 |

(Continued)

OTHER PUBLICATIONS

Kappel et al (Curr. Opin. Biol. 3: 548-553, 1992).*
Melton (BioEssays 16(9): 633-638, Sep. 1994).*
Moreadith (J Mol. Med. 75:208-216, Mar. 1997).*
Sigmund (Arterioscler. Thromb. Vasc. Biol (2000) 20(6): 1425-1429).*
Aas,T., et al, (1996). Specific P53 mutations are associated with de novo resistance to doxorubicin in breast cancer patients. Nat. Med. 2,811-814.
Adams, et al.., "The c-myc oncogene driven by immunoglobulin enhancers induces lymphoid malignancy in transgenic mice" Nature, 318 (1985) pp. 533-538.
Agrawal et al., "Antisense therapeutics: is it as simple as complementary base recognition?," Mol Med Today. Feb. 2000;6(2):72-81.
Akimitsu, N. et al. (2003) Enforced cytokinesis without complete nuclear division in embryonic cells depletinQ the activity of DNA topoisDmerase IIa. Genes to Cells 8, 393-402.

(Continued)

*Primary Examiner* — Richrad Schnizer
(74) *Attorney, Agent, or Firm* — Wilmer Cutler Pickering Hale and Dorr LLP

(57) ABSTRACT

The invention relates to recombinant vectors for inducible and/or tissue specific expression of double-stranded RNA molecules that interfere with the expression of a target gene. In certain embodiments, the invention relates to the use of Tet (tetracycline)-responsive RNA Polymerase II (Pol II) promoters (e.g., TetON or TetOFF) to direct inducible knockdown in certain cells of an integrated or an endogenous gene, such as p53. The invention also relates to a method for producing transgenic animals (e.g., mice) expressing inducible (such as tetracycline-regulated), reversible, and/or tissue-specific double-stranded RNA molecules that interfere with the expression of a target gene.

7 Claims, 6 Drawing Sheets

FOREIGN PATENT DOCUMENTS

| | | |
|---|---|---|
| WO | WO-96/36360 | 11/1996 |
| WO | WO-99/32619 | 7/1999 |
| WO | WO-99/55886 | 11/1999 |
| WO | WO-00/20025 | 4/2000 |
| WO | WO-00/67796 | 11/2000 |
| WO | WO-01/13945 | 3/2001 |
| WO | WO-01/36646 | 5/2001 |
| WO | WO-01/68836 | 9/2001 |
| WO | WO-02/16620 | 2/2002 |
| WO | WO-02/50118 | 6/2002 |
| WO | WO-02/072762 | 9/2002 |
| WO | WO-03/042382 | 5/2003 |
| WO | WO-03/093441 | 11/2003 |
| WO | WO-2004/022722 | 3/2004 |
| WO | WO-2004/035782 | 4/2004 |
| WO | WO-2004/029219 A3 | 7/2004 |
| WO | WO-2004/074445 | 9/2004 |
| WO | WO-2005/012493 | 2/2005 |
| WO | WO-2005/013886 | 2/2005 |
| WO | WO-2005/017148 | 2/2005 |
| WO | WO-2005/020969 | 3/2005 |
| WO | WO-2006/023848 | 3/2006 |
| WO | WO-2006/074186 | 7/2006 |
| WO | WO-2007/053184 | 5/2007 |
| WO | WO-2007/139985 | 12/2007 |
| WO | WO-2008/115556 | 9/2008 |
| WO | WO-2008/124133 | 10/2008 |
| WO | WO-2008/143979 | 11/2008 |
| WO | WO-2009/042798 | 4/2009 |
| WO | WO-2009/055724 | 4/2009 |

OTHER PUBLICATIONS

Alison & Lovell, "Liver cancer: the role of stem cells." Cell Prolif. vol. 38, pp. 407-421 (2005).
Anderson, Human gene therapy, (Nature 392:25-30, 1998).
Andjelkovic, et al., "Activation and phosphorylation of a pleckstrin homology domain containing protein kinase (RAC-PK/PKB) promoted by serum and protein phosphatase inhibitors" *Proc. Natl. Acad. Sci. USA*, 93, (1996) pp. 5699-5704.
Andjelkovic, et al., "Role of translocation in the activation and function of protein kinase B," *J. Biol. Chem*, 272, (1997) pp. 31515-31524.
Andoh,T. and Ishida,R. (1998). Catalytic inhibitors of DNA topoisomerase II. Biochim. Biophys. Acta 1400,155-171.
Aoki, et al., "The Akt kinase: Molecular determinants of oncogenicity." Proc. Natl. Acad. Csi.; vol. 95, pp. 14950-14955 (1998).
Arriola,E., et al., (2006). Predictive value of HER-2 and Topoisomerase IIalpha in response to primary doxorubicin in breast cancer. Eur. J. Cancer 42, 2954-2960.
Bartz et al., "Small interfering RNA Screens Reveal Enhanced Cisplatin Cytotoxicity in Tumor Cells having both BRCA Network and TP53 Disruptions," Mol. Cell. Biol., vol. 26, pp. 9377-9386 (Dec. 2006).
Bashyam et al., "Array-based comparative genomic hybridization identifies localized DNA amplifications and homozygous deletions in pancreatic cancer," Neoplasia 7, pp. 556-562 (2005).
Bass, 2001, RNA interference. The short answer, Nature 411:428-429.
Basu et al., "Akt phosphorylates the Yes-associated protein, YAP, to induce interaction with 14-3-3 and attenuation of p73-mediated apoptosis," Mol Cell 11, 11-23 (2003).
Baulcombe, Gene silencing: RNA make RNA makes no protein, 1999, Curr. Biol. 9:R599-R601.
Beard et al., "Efficient Method to Generate Single-Copy Transgenic Mice by Site-Specific Integration in Embyonic Stem Cells," Genesis, vol. 44: pp. 23-28 (2006).
Bern et al., A Functional genetic approach identifies the PI3K pathway as a major determinant of trastuzumab resistance in breast cancer, Cancer Cell, vol. 12, pp. 395-402, (2007).
Berns et al., "A Alrge-scale RNAi screen in human Cells identifies new components of the p53 pathway," Nature, vol. 428, pp. 431-437 (Mar. 2004).
Billy, et al., "Specific interference with gene expression induced by long, double-stranded RNA in mouse embryonal teratocarcinoma cell lines," PNAS, 98(25):14428-14433 (2001).

Block et al., "Population expension, clonal growth, and specific differentiation patterns in primary cultures of hepatocytes induced by HGF/SF, EGF and TGE alpha in a chemically defined (HGM) medium," J. Cell Biol. 132, 1133-1149 (1996).
Boonsong, A. et al. (2000) Characterization of the Topoisomerase I Locus in Human Colorectal Cancer. Cancer Genet Cytoaenet 121, 56-60.
Bortul et al., Constitutively active Akt1 protects HL60 leukemia Bortul et al., "Constitutively active Akt1 protects HL60 leukemia cells from TRAIL-induced apoptosis through a mechanism involving NF-kappaB activation and cFLIP(L) upregulation," Leukemia: Official Journal of the Leukemia Society of America, Leukemia Research Fund, 17:379-389 (2003).
Brennan, et al, "Phosphatidylinositol 3-kinase is essential for the proliferation of lymphoblastoid cells" *Oncogene*, 21, (2002) pp. 1263-1271.
Brezinova, J. et al. (2005) Prognostic significance of del(20q) in patients with hematological malignancies. Cancer Genetics and Cytogenetics 160,188-192.
Brummelkamp, T. R. et al. (2006) an shRNA barcode screen provides insight into cancer cell vulnerability to MDM2 inhibitors Nat. Chem. Biol. 2, 202-206.
Buske et al, Deregulated expression of HOXB4 enhances the primitive growth activity of human hematopoietic cells, Blood 100(3):862-868, 2002.
Caplen, RNAi as a gene therapy approach, (Expert Opin. Biol. Ther. 2003, vol. 3, pp. 575-586).
Carey, et al., "Role of phosphatidylinositol 3-kinase in anti-IgM- and anti-IgD-induced apoptosis in B cell lymphomas" *J. Immunol*, 166, (2001) pp. 1618-1626.
Cejka et al, Short interfering RNA (siRNA): tool or therapeutic?, (Clinical Science 110: 47-58, 2006).
Check, RNA to the rescue?, (Nature, 2003, vol. 425, pp. 10-12).
Chen et al., "Co-expression and regulation of Met and Ron proto-oncogenes in human hepatocellular carnicoma tissues and cell lines," Hepatology, vol. 26, pp. 59-66 (1997).
Cheng, et al., "Sustained gene expression in retrovirally transduced, engrafting human hematopoietic stem cells and their lympho-myeloid progeny" *Blood* 92, (1998) pp. 83-92.
Comerford et al., "Induction of Hepatocyte proliferation and deathe by modulation of T-antigen expression," Oncogene, vol. 22, pp. 2515-2530 (2002).
Crook et al., "An apoptosis-inhibiting baculovirus gene with a zinc finger-like motif," J. Virol 67, 2168-2174 (1993).
Crump et al., "Phase I trial of sequential topotecan followed by etoposide in adult with myeloid leukemia: a National Cancer Instute of Canada Clinical Trials Group Study," Leukemia, vol. 13, pp. 343-347 (1999).
Cullen R., "RNAi the natural way," Nature Genetics, vol. 37, pp. 1163-1165 (Nov. 2005).
Dacquin et al., "Mouse α1(I)-Collagen Promotor is the best known Promoter to drive efficient Cre Recombinase Expression in Osteoblast," Developmental Dynamics vol. 224, pp. 245-251 (2002).
Dai et al., "A comprehensive search for DNA amplification in lung cancer identifies inhibitors of apoptosis cIAP1 and cIAP2 as candidates oncogenes," Human Molecular genetics, vol. 12, No. 7, pp. 791-801 (Apr. 2003).
Datta, et al., "Cellular survival: A play in three akts" *Genes Dev*. 13, (1999) pp. 2905-2927.
De Benedetti et al., "eIF-4E expression and its role in malignancies and metastases," Oncogene 23: 3189-3199 (2004).
De Miguel, et al., Dissection of the c-Kit signaling pathway in mouse primordial germ cells by retroviral-mediated gene transfer.; PNAS vol. 99, No. 16 pp. 10458-10463.
De Stanchina, et al., "E1A signaling to p53 involves the p19(ARF) tumor suppressor" *Genes. Dev*., 12, (1998) pp. 2434-2442.
Devroe et al., Retrovirus-delivered siRNA (BMC Biotechnology, 2000 vol. 2:1-5).
Di Cristofano et al., "Pten and p27KIP1cooperate in prostate cancer tumor suppression in the mouse," Nature Genetics 27: 222-224 (2001).
Di Cristofano, et al., "Pten is essential for embryonic development and tumor suppression" *Nature Genetics*, 19, (1998) pp. 348-355.

Dickins et al., "Probing Tumor Phenitypes Using Stable and Regulated Synthetic MicroRNA Precursors," Nature Genetics, 37(11):1289-1295 (2005).

Dimri,G.P., et al., (2002). The Bmi-1 oncogene induces telomerase activity and immortalizes human mammary epithelial cells. Cancer Res. 62,4736-4745.

Duckett et al., "A conserved family of cellular genes related to the baculovirus iap gene and encoding apoptosis inhibitors," EMBO J. 15, 2685-2694 (1996).

Duncan S.A., "Generation of Embryos directly from embryonic stem cells by tetraploid embryo complementation reveals a role for GATA factors in organogenesis," Biochemical Society Transactions, vol. 33, pp. 1535-1536 (2005).

Dupraz, et al., "Lentivirus-medicated Bcl-2 expression in bTC-tet cells improves resistance to hypoxia and cytokine-induced apoptosis while preserving in vitro and in vivo control of insulin secretaion," Gene Therapy, 6:1160-1169 (1999).

Edinger, et al., "Akt maintains cell size and survival by increasing mTOR-dependent nutrient uptake" *Mol. Biol. Cell*, 13, (2002) pp. 2276-2288.

Elbashir et al., Analysis of gene function in somatic mammalian cells using small interfering RNAs, Methods 26:199-213 (2002).

Elbashir, et al., "Functional anatomy of siRNA for mediating efficient RNAi in *Drosophila melanogaster* embryo lysate," The EMBO Journal, 20 (23):6877-6888 (2001).

Farmer,H., et al., (2005). Targeting the DNA repair defect in BRCA mutant cells as a therapeutic strategy. Nature 434,917-921.

Fire et al, 1998, Potent and specific genetic interference by double-stranded RNA in *Caenorhabditis elegans*, Nature 391:806-811.

Fire, 1999, RNA-triggered gene silencing, Trends Genet. 15:358-363.

Fortune,J.M. and Osheroff,N. (2000). Topoisomerase II as a target for anticancer drugs: when enzymes stop being nice. Prog. Nucleic Acid Res. Mol. Biol. 64,221-253.

Fux et al., "Streptogrmin-and tetra-cycline-responsive dual regulated expression of p27$^{kip1}$ sense and antisense enables positive and negative growth control of Chinese hamster ovary cells," Nucl. Acid. Res., vol. 29(4); pp. e19-e25 (2001).

Glinsky,G.V., et al. (2005). Microarray analysis identifies a deathfrom-cancer signature predicting therapy failure in patients with multiple types of cancer. J. Clin. Invest 115,1503-1521.

Graff et al., "Translational control and metastatic progression: Enhanced activity of the mRNA cap-binding protein E1F-4E selectively enhances translation of metastasis-related mRNAs," Clinical & Experimental Metastasis 20: 265-273 (2003).

Grellier et al., "Expression of insulin-like Growth Factor-binding protein 6 complementary DNA Alters Neuroblastoma cell growth," Cancer Res., vol. 58, pp. 1670-1676 (1998).

Grellier et al., "Expression of Insulin-like Growth Factor-binding protein 6 Complementary DNA Alters Neuroblastoma Cell Growth," Cancer Research, vol. 58, pp. 1670-1676 (1998).

Griffin et al., "Down-Regulation of Regulatory Subunit Type 1A of protein Kinase A Leads to endocrine and other Tumors," Cancer Res., vol. 64, pp. 8811-8815 (2004).

Grolleau, et al., "Global and specific translational control by rapamycin in T cells uncovered by microarrays and proteomics" *J. Biol. Chem.* 277, (2002) pp. 22175-22184.

Gros et al. (1986) Isolation and expression of a complementary DNA that confers multidrug resistance. Nature 323:23, 728-731.

Gros et al., "Identification of New Drug Sensitivity Genes Using Genetic Suppressor Elements," Cancer REs., vol. 63, pp. 164-171 (Jan. 1, 2003).

Grunwald, et al., "Inhibitors of mTOR reverse doxorubicin resistance conferred by PTEN status in prostate cancer cells" *Cancer Res.*, 62 (2002) pp. 6141-6145.

Gudkov et al., "Cloning mammalian genes by expression selection of genetic suppressor elements," Proc. Natl. Acad. Sci. USA, vol. 91, pp. 3744-3748 (Apr. 1994).

Gudkov,A.V et al., (1993). Isolation of genetic suppressor elements, inducing resistance to topoisomerase II-interactive cytotoxic drugs, from human topoisomerase II cDNA. Proc. Natl. Acad. Sci. U. S. A 90,3231-3235.

Guo et al., "Liver repopulation after cell transplantation in mice treated with retrosine and carbon tetrachloride." Transplantation vol. 73, pp. 1818-1824 (2002).

Gupta,M., et al., (1997). Inactivation of p53 increases the cytotoxicity of camptothecin in human colon HCT116 and breast MCF-7 cancer cells. Clin. Cancer Res. 3, 1653-1660.

Haghighat, et al., "The eIF4G-eIF4E complex is the target for direct cleavage by the rhinovirus 2A proteinase" *J. Virol.*, 70 (1996) pp. 8444-8450.

Hammond et al., "A Phase I and Translational Study of Sequential Administration of the Topoisoerase I and II Inhibitors Topotecan and Etoposide," Clinical Cancer Research, vol. 4, pp. 1459-1467 (Jun. 1998).

Hanahan, et al., "The hallmarks of cancer," *Cell*, 100 (2000) pp. 57-70.

Hannon, G. J. (2002) RNA interference Nature 418, 244-251.

Harris, et al., "The E mu-myc transgenic mouse. A model for high-incidence spontaneous lymphoma and leukemia of early B cells" *J. Exp. Med.*, 167, (1988) pp. 353-371.

Hawley, et al., "Thrombopoietic potential and serial repopulating ability of murine hematopoietic stem cells constitutively expressing interleukin 11" Proc. Natl. Acad. Sci. USA, 93, (1996) pp. 10297-10302.

Hemann et al., "An epi-allelic series of p53 hypomorphs created by stable RNAi produces distinct tumor phenotypes in vivo," Nature Genetics, Nature America, New York, vol. 33, pp. 396-400 (Mar. 2003).

Hemann, T. et al. (2004) Suppression of tumorigenesis by the p53 target PUMA. PNAS 101 :25,9333-9338.

Hideshima, et al., "Biologic sequelae of interleukin-6 induced PI3-K/Akt signaling in multiple myeloma" *Oncogene*, 20, (2001) pp. 5991-6000.

Hirao, A. et al. (2002) Chk2 Is a Tumor Suppressor That Regulates Apoptosis in both an Ataxia Telangiectasia Mutated (ATM)-Dependent and an ATM-Independent Manner. Molecular and Cellular Biology 22:18,6521-6532.

Hormuzdi et al., "A gene-targeting Approach Identifies a Function for the First Intron in Expression of the α1 (I) Collagen Gene," Molecular and cellular Biology, vol. 18, pp. 3368-3375 (Jun. 1998).

Hosoi, et al., "Rapamycin causes poorly reversible inhibition of mTOR and induces p53-independent apoptosis in human rhabdomyosarcoma cells," *Cancer Res.*, 59, (1999) pp. 886-894.

Hsiang,Y.H. and Liu,L.F. (1988). Identification of mammalian DNA topoisomerase I as an intracellular target of the anticancer drua camotothecin. Cancer Res. 48, 1722-1726.

Hsiang,Y.H., et al. (1985). Camptothecin induces protein- . linked DNA breaks via mammalian DNA topoisomerase I. J. Biol. Chem. 260,14873-14878.

Hsu, et al. "The AKT kinase is activated in multiple myeloma tumor cells" *Blood*, 98, (2001) pp. 2853-2855 (2001).

Hu et al., "Association of Vimentin overexpression and hepatocellular carcinoma metastasis," Oncogene 23, 298-302 (2004).

Hu,T., et al. (2002). ATPase domain of eukaryotic DNA topoisomerase II. Inhibition of ATPase activity by the anti-cancer drug bisdioxopiperazine and ATP/ADP-induced dimerization. J. Biol. Chem. 277,5944-5951.

Hu,X., et al. (2006). Stable RNA interference of ErbB-2 gene synergistic with epirubicin suppresses breast cancer growth in vitro and in vivo. Biochem. Biophys. Res. Commun. 346,778-785.

Huang et al., "The Hippo signaling pathway coordinately regulates cell proliferation and apoptosis by inactivating Yorkie, the drosophila Homolog of YAP," Cell 122, 421-434 (2005).

Huang, et al., "Targeting mTOR signaling for cancer therapy" *Curr Opin. Pharmacol.*, 3, (2003) pp. 371-377.

Huesken, D. et al. (2005) Design of a genome-wide siRNA library using an artificial neural network Nat. Biotechnol. 23, 995-1001.

Huisman et al., "A phase I study of sequential intravenous topotecan and etoposide in lung cancer patients," Annals of Oncology, vol. 12, pp. 1567-1573 (2001).

Hunter, 1999, Genetics: a touch of elegance with RNAi, Curr. Biol. 9:R440-R442.

Hyun, et al., "Loss of PTEN expression leading to high Akt activation in human multiple myelomas" *Blood*, 96, (2000) pp. 3560-3568.

Imoto et al., Identification of CIAP1 as a candidate target gene within an amplicon at 11q22 in esophageal squamous cell carcinomas, Cancer Res. 61, 6629-6634 (2001).

International Search Report and Writen Opinion mailed Jun. 11, 2008 for International Application No. PCT/US07/012592 filed May 23, 2007.

International Search Report and Written Opinion mailed Oct. 8, 2008, for International Patent Application No. PCT/US08/03691 filed Mar. 19, 2008.

International Search Report and Written Opinion mailed on May 10, 2007 for International Application No. PCT/US06/021062 filed on May 31, 2006.

International Search Report and Written Opinion mailed on Sep. 17, 2008 for International Application No. PCT/US07/18061 filed on Aug. 15, 2007.

International Search Report mailed Jan. 19, 2009 for International Patent Application No. PCT/US08/06293 filed May 16, 2008.

Iorns, E., Lord, C. J., Turner, N. & Ashworth, A. (2007) Utilizing RNA interference to enhance cancer druq discovery Nat. Rev. Druq Discov. 6, 556-568.

Jacobs,J.J., et al.,(1999). Bmi-1 collaborates with c-Myc-in tumorigenesis by inhibiting c-Myc-induced apoptosis via INK4a/ARF. Genes Dev. 13,2678-2690.

Johnstone, et al., "Apoptosis: A link between cancer genetics and chemotherapy" *Cell* 108 (2002) pp. 153-164.

Jones et al,Protein Kinase B Regulates T Lymphocyte Survival, Nuclear Factor kB Activation, and Bcl-XL Levels In Vivo, J. Exp. Med. 191(10):1721-1733,2000.

Jung et al., "Adenovirus-medited transfer of siRNA against PTTG1 inhibits liver cancer cell growth in vitro and in vivo," Hepatology; vol. 43, pp. 1042-1052 (2006).

Kim et al, Radiation enhancement by the combined use of topoisomerase I inhibitors, RFS-2000 or CPT-11, and topoisomerase II inhibitor etoposide in human lung cancer cells, (Radiother. Onc. 62: 61-67, 2002).

Langdon, et al., "The c-myc oncogene perturbs B lymphocyte development in E-mu-myc transgenic mice" *Cell*, 47, (1986) pp. 11-18.

Lazaris-Karatzas, et al., "Malignant transformation by a eukaryotic initiation factor subunit that binds to mRNA 5' cap," *Nature*, 345, (1990) pp. 544-547.

Lee et al., Maternal or paternal exposure to radiation increases susceptibility to the induction of glutathione S-transferasepositive hepatic foci in offspring rats.Cancer Lett. Oct. 23, 1998;132(1-2):31-6.

Lee et al., 2002. Expression of small interfering RNAs targeted against HIV-1 rev transcripts in human cells, Nat. Biotech. 20:500-505.

Lee et al., MicroRNA maturation: stepwise processing and subcellular localization, EMBO J. 21: 4663-4670, 2002.

Leung et al., "A Method for random mutagenesis of a defined DNA segment using a modified polymerase chain reaction," Technique 1:11-15 (1989).

Lewis et al., 2002, Efficient delivery of siRNA for inhibition of gene expression in postnatal mice, Nat. Genet. 32:107-108.

Liston et al., "Suppression of apoptosis in mammalian cells by NAIP and a related family of IAP genes," Nature 379, pp. 349-353 (1996).

Liston et al., "The inhibitors of apoptosis: there is more to life than Bcl2," Oncogene 22, pp. 8568-8580 (2003).

Liu et al, Overexpression of Bcl-xL Promotes Chemotherapy Resistance of Mammary Tumors in a Syngeneic Mouse Model, Am. J. Pathol. 155(6):1861-1867, 1999.

Liu,L., Andrews,L.G., and Tollefsbol,T.O. (2006). Loss of the human polycomb group protein BMI1 promotes cancer-specific cell death. Oncoqene 25,4370-4375.

Llovet etal. "Hepatocellular carcinoma." Lancet, vol. 362, pp. 1907-1917 (2003).

Lottmann et al., "The Tet-On system in transgenic mice: inhibition of the mouse pdx-1 gene activity by antisense RNA expression in pancreatic β-cells," J. Mol Med, vol. 79, pp. 321-328 (2001).

Lowe,SW., et al. (1994). p53 status and the efficacy of cancer therapy in vivo. Science 266, 807-810.

Lowe,SW., et al. (1993). p53-dependent apoptosis modulates the cytotoxicity of anticancer aqents. Cell 74, 957-967.

Lucito et al., "Representational oligonucleotide microarray analysis: a high-resolution method to detect genome copy number variation." Genome Res. vol. 13, pp. 2291-2305 (2003).

Mangi et al., "Mesenchymal stem cells modified with Akt prevent remodeling and restore performance of infarcted hearts," *Nature Medicine*, 9:1195-1201 (2003).

Mano, M.S. et al. (2006) The 17q12-q21 amplicon: HerZ and topoisomerase-IIa and their importance to the biology of solid tumours. Cancer Treatment Reviews 33,64-77.

Mao, Y. et al. (1999) Mutations of human topoisomerase II alpha affecting multidrug resistance and sensitivity Biochemistry 38, 10793-10800.

Marius Sudol et al., "Characterization of the Mammalian YAP (Yes-associated Protein) Gene and Its Role in Defining a Novel Protein Module, the WW Domain," The Journal of Biological Chemisrty, vol. 270, pp. 14733-14741 (1995).

Masuda et al, CPT: A New Derivative of Camptothecin for the Treatment of Refractory or Relapsed Small-Cell Lung Cancer, (J. Clin. Onc. 10(8): 1225-1229, 1992).

Masuda, Combination of Irinotecan and Etoposide for Treatment of Refractory or Relapsed Small-Cell Lung Cancer, (J. Clin. Onc. 16(10): 3329-3334,1998).

Mayeur et al., "Malignant transformation by the eukaryotic translation initiation factor 3 subunit p48 (eIF3e)," FEBS Letters 514, pp. 49-54 (2002).

Mayo et al., "PTEN protects p53 from Mdm2 and sensitizes cancer cells to chemotherapy," J. Cell Biol. vol. 277, pp. 5484-5489 (2002).

McCurrach, et al., "bax-deficiency promotes drug resistance and oncogenic transformation by attenuating p53-dependent apoptosis" *Proc. Natl. Acad. Sci. USA*, 94 (1997) pp. 2345-2349.

McCurrach, et al., "Methods for studying pro- and antiapoptotic genes in nonimmortal cells"*Methods Cell Biol.*, 66, (2001) pp. 197-227.

Miao, Z. et al. (2006) 4-Nitroquinoline-1-0xide Induces the Formation of Cellular Topoisomerase I-DNA Cleavaqe Complexes. Cancer Res 66:13, 6540-6545.

Miller et al, Feasibility of Using Autologous Transplantation to Evaluate Hematopoietic Stem Cell-Based Gene Therapy Strategies in Transgenic Mouse Models of Human Disease, Mol. Therapy 6(3):422-428, 2002.

Min, et al., "Constitutive phosphorylation of Akt/PKB protein in acute myeloid leukemia: its significance as a prognostic variable," *Leukemia* 17: 995-997 (2003).

Montgomery et al., 1998, RNA as a target of double-stranded RNA-mediated genetic interference in *Caenorhaditis elegans*, PNAS, 95:15502-15507.

Morham,S.G., Kluckman,K.D., Voulomanos,N., and Smithies,O. (1996). Targeted disruption of the mouse topoisomerase I qene by camptothecin selection. Mol. Cell Biol. 16, 6804-6809.

Morino, et al., "Eukaryotic translation initiation factor 4E (eIF4E) binding site and the middle one-third of eIF4GI constitute the core domain for cap-dependent translation, and the C-terminal one-third functions as a modulatory region" *Mol Cell Biol.* 20, (2000) pp. 468-477.

Mousses, et al., "RNAi microarray analysis in cultured mammalian cells" *Genome Res.*, 13, (2003) pp. 2341-2347.

Mukhopadhyay,U.K., et al.. (2005). RNA silencing of checkpoint regulators sensitizes p53-defective prostate cancer cells to chemotherapy while sparinq normal cells. Cancer Res. 65, 2872-2881.

Nadler, et al., B4, A Human B Lymphocyte-Associated antigen expressed on normal, mitogen-activated, and malignant B lymphocytes, J. Immunol., 131:244-250 (1983).

Neri et al., "The phosphoinositide 3-kinase/AKT1 pathway involvement in drug and alltrans-retinoic acid resistance of leukemia cells," *Molecular Cancer Research*, 1:234-246 1(2003).

Neshat, et al., "Enhanced sensitivity of PTEN-deficient tumors to inhibition of FRAP/mTOR," *Proc. Natl. Acad. Sci. USA*, 98, (2001) pp. 10314-10319.

Ngo,V.N., et al.,(2006). A loss-of-function RNA interference screen for molecular targets in cancer. Nature 441, 106-110.

Nguyen et al, RNAi therapeutics: An update on delivery, (Curr. Opin. Mol. Ther. 10(2): 158-167,2008).

Nitiss, J. et al. (1988) DNA Topoisomerase-Targeting Antitumor Drugs Can Be Studied in Yeast. Proceedings of the National Academy of Sciences of the United States of America 85:20, 7501-7505.

Nitou et al., "Purification of fetal mouse hepatoblasts by magnetic beads coated with monoclonal anti-e-cadherin antibodies and their in vitro culture." Exp. Cel Res. vol. 279, pp. 330-343 (2002).

Oguro, et al., "RNA aptamers to initiation factor 4A helicase hinder cap-dependent translation by blocking ATP hydrolysis" RNA, 9 (2003) pp. 394-407.

Opalinska et al, Nucleic-acid therapeutics: basic principles and recent applications, (Nature Reviews Drug Discovery, 2002, vol. 1, pp. 503-514).

Overholtzer et al., "Transforming properties of YAP, a candidate oncogene on the chromosome 11q22 amplicon," PNAS, vol. 103, pp. 12405-12410 (Aug. 15, 2006).

Paddison et al., "A Resource for large-scale RNA-interference-based screens in mammals," Nature, vol. 428, pp. 427-431 (Mar. 2004).

Paddison et al., 2002, RNA interference: The new somatic cell genetics? Cancer Cell 2:17-23.

Paddison et al., 2002, Short hairpin RNAs (shRNAs) induce sequence-specific silencing in mammalian cells, Genes Dev. 16(8):948-958.

Padilla-Noriega, et al., "Rotavirus protein NSP3 shuts off host cell protein synthesis" Virology, 298 (2002) pp. 1-7.

Pang,E.,et al., (2005). Karyotypic imbalances and differential gene expressions in the acquired doxorubicin resistance of hepatocellular carcinoma cells. Lab Invest 85, 664-674.

Parkin et al. "Estimating the world cancer burden: Globocan 2000." Int. J. Cancer vol. 94, pp. 153-156 (2001).

Peng et al., "Amplification of the c-myc gene in human hepatocellular carcinoma: biological significance," J. Formos. Med Assoc. 92, 866-870 (1993).

Plas, et al., "Akt and Bcl-xL promote growth factor-independent survival through distinct effects on mitochondrial physiology," J. Biol. Chem., 276, (2001) pp. 12041-12048.

Podsypanina, et al., "An inhibitor of mTOR reduces neoplasia and normalizes p70/S6 kinase activity in Pten+/−mice," Proc Natl. Acad. Sci. USA, 98, (2001) pp. 10320-10325.

Polunovsky, et al., "Translational control of the antiapoptotic function of Ras," J. Biol. Chem. 275, (2000) pp. 24776-24780.

Pouton et al, Key issues in non-viral gene delivery, (Adv. Drug Del. Rev. 46: 187-203,2001).

Pyronnet, et al., "Human eukaryotic translation initiation factor 4G (eIF4G) recruits Mnk1 to phosphorylate eIF4E" EMBO J., 18 (1999) pp. 270-279.

R.-Borlado, et al., "Increased phosphoinositide 3-kinase activity induces a lymphoproliferative disorder and contributes to tumor generation in vivo" FASEB J, 14, (2000) pp. 895-903.

Rabbani et al., "Regulation in vivo of the growth of Leydig Cell Tumors by Antisense Ribonucleic Acid for Parathyroid Hormone-Related peptide," Endocrinology, vol. 136, pp. 5416-5422 (1995).

Rabbani et al., "Regulation in vivo of the growth of Leydig cell tumors by antisense ribonucleic Acid for parathyroid hormone-related peptide," Endocronology, vol. 136, pp. 5416-5422 (1995).

Rajasekhar, et al., "Oncogenic Ras and Akt signaling contribute to glioblastoma formation by differential recruitment of existing mRNAs to polysomes," Mol. Cell., 12, (2003) pp. 889-901.

Read et al, Barriers to Gene Delivery Using Synthetic Vectors, (Adv. Gen. 53:19-46, 2005).

Reed, Bcl-2 Family Proteins: Regulators of Apoptosis and Chemoresistance in Hematologic Malignancies, Sem. Hematology 34 (4 Supp. 5):9-19, 1997.

Reidhaar-Olson, et al., "Combinatorial cassette mutagenesis as a probe of the informational content of protein sequences" Science, 241, (1988) pp. 53-57.

Rottenberg, S. et al. (2007) Selective induction of chemotherapy resistance of mammary tumors in a conditional mouse model for hereditary breast cancer Proc. Natl. Acad. Sci. U. S. A 104,12117-12122.

Roymans, et al., "Phosphatidylinositol 3-kinases in tumor progression" Eur J Biochem, 268, (2001) pp. 487-498.

Rubison et al., "A lentivirus-based system to functionally silence genes in primary mammalian cells, stem cells and transgenic mice by RNA interference," Nature Genetics vol. 33, pp. 401-407 (2003).

Sakai, et al., "PTEN gene alterations in lymphoid neoplasms," Blood, 92, (1998) pp. 3410-3415.

Samuelson, et al., "Selective induction of p53 and chemosensitivity in RB-deficient cells by E1A mutants unable to bind the RB-related proteins" Proc. Natl. Acad. Sci. USA., 94, (1997) pp. 12094-12099.

Sandgren et al., "Oncogene-induced liver neoplasia in transgenic mice." Oncogene, vol. 4 pp. 715-724. (1989).

Scanlon, "Anti-Genes: siRNA, Ribozymes and Antisense," Current Pharmaceutical Biotechnoloqy, 5:415-420 (2004).

Scherer and Rossi, Approaches for the sequence-specific knockdown ofmRNA, Nature Biotechnology vol. 21 pp. 1457-1465 (2003).

Schimmer et al., "Targeting the IAP Family of Caspase Inhibitors as an emerging Terapeutic Strategy," Hematology/the Education program of the American Society of Hematology. Education program 2005, pp. 215-219.

Schimmer, "Inhibitor of apoptosis proteins: Translating basic knowledge into clinical practice," Cancer Research 64, pp. 7183-7190 (2004).

Schmelzle, et al., "TOR, a central controller of cell growth," Cell., 103, (2000) pp. 253-262.

Schmidt, et al., "Dissecting p53 tumor suppressor functions in vivo," Cancer Cell, vol. 1, pp. 289-298 (2002).

Schmitt et al., "A senescence program controlled by p53 and P161NK4a contributes to the outcome of cancer therapy," Cell, 109:335-346 (2002).

Schmitt, et al., "Bcl-2 Mediates chemoresistance in matched pairs of primary Eu-myc lymphomas in vivo" Blood Cells Mol Dis., 27 (2001) pp. 206-216.

Schmitt, et al., "Genetic analysis of chemoresistance in primary murine lymphomas" Nat. Med, 6, (2000) pp. 1029-1035.

Schmitt, et al., "INK4a/ARF mutations accelerate lymphomagenesis and promote chemoresistance by disabling p53" Genes Dev., 13, (1999) pp. 2670-2677.

Schwarts et al., "Targeting the cell cycle: a new approach to cancer therapy," Journal of Clinical Oncology 23: 9408-9421 (2006).

Sebat et al., "Large-scale copy number polymorphism in the human genome." Science vol. 305, pp. 525-528 (2004).

Seilber et al., "Single shRNA configuration for ubiquitious gene knockdown in mice," Nucl. Acids Res., vol. 33, pp. e67, published onlie Apr. 24, 2005.

Serrano, et al., "Oncogenic ras provokes premature cell senescence associated with accumulation of p53 and p161NK4A" Cell, 88 (1997) pp. 593-602.

Serrano, et al., "Role of the INK4a locus in tumor suppression and cell mortality" Cell, 85 (1997) pp. 27-37.

Shah, N. P. et al. (2002) Multiple BCR-ABL kinase domain mutations confer polyclonal resistance to the tyrosine kinase inhibitor imatinib (STI571) in chronic phase and blast crisis chronic myeloid leukemia Cancer Cell 2, 117-125.

Sharp, 1999, RNAi and double-strand RNA, Genes Dev. 13:139-141.

She et al., "Resistance to Gefitinib in PTEN-Null HER-Overexpressing tumor Cells can be overcome through restoration of PTEN Fuction or Pharmacologic Modulation of Constitutive Phosphatidylinositol 3'-kinase/Akt pathway signaling," Clinical Cancer Research, vol. 9, 4340-4346 (Oct. 2003).

Sherr Charles, "The INKaI ARF Network in Tumor Suppression," Molecular Cell Biology , pp. 731-737 (2001).

Shi et al, "Synergetic anticancer effect of combined quercetin and recombinant adenoviral vecto expressing human wild-type p53, GM-Csf, and B7-1 genes on hepatocellular carcinoma cells in vitro," World J Gastroenterol, vol. 9, pp. 73-78 (2003).

Siegmund et al, Selective Inhibition of FLICE-like Inhibitory Protein (FLIP) Expression With Small Interfering RNA Oligonucleotides (siRNAs) Is Sufficient to Sensitize Tumor Cells for TRAIL-Induced Apoptosis, (Mol. Med. 8(11): 2002).

Silke et al., "Determination of cell survival by RING-mediated regulation of inhibitor of apoptosis (IAP) protein abundance," Proc. Natl. Acad. Sci. USA 102, 16182-16187 (2005).

Silva et al., "Second-generation ShRNA libraries covering the mouse and human genomes," nature Genetics, nature America, New York, US, vol. 37, pp. 1281-1288 (Oct. 2005).

Siolas et al., "Synthetic ShRNAs as potent RNAi triggers," Nature Biotechnology, vol. 23, pp. 227-231 (Feb. 2005).

Sioud,"On the delivery of small interfering RNAs into mammalian cells," (Exp. Opin. Drug Deliv. 2(4): 639-651, 2005).

Snijders et al., "Rare amplicons implicate frequent deregulation of cell fate specification pathways in oral squamous cell carcinoma," Oncogene 24, 4232-4242 (2005).

Steck, et al., "identification of a candidate tumor suppressor gene, MMAC1, at chromosome 10q23.3 that is mutated in multiple advanced cancers" *Nat. Genet.*, 15 (1997) pp. 356-362.

Stegmeier et al., "A lentiviral microRNA-based system for single-copy polymerase II-regulated RNA interference in mammalian cells," PNAS, vol. 102, pp. 13212-13217 (Sep. 2005).

Strano et al., "Physical interaction with YEs-associated protein enhances p73 transcriptional activity," J. Biol Chem 276, pp. 15164-15173 (2001).

Strasser A. et al. (1994) DNA Can Induce Apoptosis in Proliferating Lymphoid Cells via p53-Independent Mechanisms Inhibitable by Bcl-2. Cell 79, 329-339.

Sudol, "Yes-associated protein (YAP65) is a proline-rich phosphoprotein that binds to the SH3 domain of the Yes proto-oncogene product," Oncogene 9, 2145-2152 (1994).

Suzuki, "High cancer susceptibility and embryonic lethality associated with mutation of the PTEN tumor suppressor gene in mice" *Current Biology*, 8 (1998) pp. 1169-1178.

Takai,H.,et al., (2002). Chk2-deficient mice exhibit radioresistance and defective p53-mediated transcription. EMBO J. 21, 5195-5205.

Takimoto et al., "Augmentation of antitumor effects of p53 gene therapy by combination with HDAC inhibitor," Cancer Biol & Ther, vol. 4, pp. 421-428 (2005).

Tanner,M., et al., (2006). Topoisomerase IIalpha gene amplification predicts favorable treatment response to tailored and dose-escalated anthracycline-based adjuvant chemotherapy in HER-2/neu-amplified breast cancer: Scandinavian Breast Group Trial 9401. J. Clin. Oncol. 24, 2428-2436.

Tavernarakis et al., "Heritable and Inducible Genetic Interference by double-Stranded RNA Encoded by Transgenes," Nature Genetics, 24:180-183 (2000).

Thompson and Lyons, "Recent progress in targeting the Raf/MEK/ERK pathway with inhibitors in cancer drug discovery," Current Opinion in Pharmacology 5: 350-356 (2005).

Thorgeirsson, "Hepatic stem cells in liver regeneration," FASEB J. 10, 1249-1256 (1996).

Topisirovic et al., "Aberrant Eukaryotic Translation Initiation Factor 4E-Dependent mRNA Transport Impedes Hematopoietic Differentiation and Contributes to Leukemogenesis," Molecular and Cellular Biology, vol. 23, pp. 8992-9002 (2003).

Trigueros, S. et al. (2002) Failure to Relax Negative Supercoiling of DNA Is a Primary Cause of Mitotic Hyper-recombination in Topoisomerase-deficient Yeast Cells. The Journal of Biological Chemistry 277:40, 37207-27211.

Tuma, 2003, Antisense and RNAi: the gloves are off. Biotech. Annual Review, BioMedNet 5:1-2.

Tuschl, et al., "Small Interfering RNAs: A revolutionary tool for the analysis of gene function and gene therapy,"Molecular Interventions, American Society for Pharmacology and Experimental Therapeutic, 2(3):158-167 (2002).

Uemura, T. et al. (1984) Isolation of type I and II DNA topoisomerase mutants from fission yeast: single and double mutants show different phenotypes in cell growth and chromatic organization. The EMBO Journal 3:8,1737-1744.

Urlinger et al., "Exploring the sequence space for etracycline dependent transcriptional activators: Novel mutations yield expanded range and sensitivity," PNAS (2000), vol. 97, pp. 7963-7968.

Van Parjis, et al., "Uncoupling IL-2 signals that regulate T cell proliferation, survival, and Fas-mediated activation-induced cell death" *Immunity*, 11, (1999) pp. 281-288.

Verma et al, Gene therapy—promises, problems and prospects, (Nature 389: 239-242, 1997).

Viera, et al., Rituximab for Reduction of Anti-HLA Antibodies in Patients Awaiting Renal Transplantation: 1. Safety, Pharmacodynamics, and Pharmacokinetics, Transplantation, 2004 77:542.

Villman,K.,et al., (2006). TOP2A and HER2 gene amplification as predictors of response to anthracycline treatment in breast cancer. Acta Oncol. 45, 590-596.

Vivanco, et al., "The Phosphatidylinositol 3-Kinase AKT pathway in human cancer" *Nat. Rev. Cancer*, 2, (2002) pp. 489-501.

Wang et al., "Activation of the Met receptor by cell attachment induces and sustains hepatocellular carcinomas in transgenic mice.", J. Cell Biol. vol. 153 pp. 1023-1034 (2001).

Wang et al.,"Stable and controllable RNA interference: investigating the physiological function of glutathionylated actin," Proc. NAt. Acad. Sci., vol. 100(9); pp. 5103-5106 (2003).

Wang, James C. (2002) Cellular Roles of DNA Topoisomerases: A Molecular Perspective Nature 3, 430-441.

Wang,Y., Zhu,S., Cloughesy,T.F., Liau,L.M., and Mischel,P.S. (2004). p53 disruption profoundly alters the response of human glioblastoma cells to DNA topoisomerase I inhibition. Oncoqene 23,1283-1290.

Watkins et al., "Translation initiation and its deregulation during tumorigenesis," British Journal of cancer, vol. 86, pp. 1023-1027 (2002).

Wendel HG, "In vivo RNAi library screen to identify mediators of disease progression and drug resistance in CML," Report for U.S. Army Medical Research and material Command, Sep. 2006.

West et al., "Activation of the P13K1Akt pathway and chemotherapeutic resistance," *Drug Resistance Updates*, 5:234-248 (2002).

Whitacre et al, Topotecan Increases Topoisomerase IIα Levels and Sensitivity to Treatment with Etoposide in Schedule-dependent Process, (Cancer Res. 57: 1425-1428, 1997).

Whitehurst, A. W. et al. (2007) Synthetic lethal screen identification of chemosensitizer loci in cancer cells Nature 446,815-819.

Wianny et al., 2000, Specific interference with gene function by double-stranded RNA in early mouse development, Nat. Cell. Biol. 2:70-75.

Witt, A. et al. (2006) Functional Proteomics Approach to Investigate the Biological Activities of cDNAs Implicated in Breast Cancer. Journal of Proteome Research 5, 599-610.

Woodworth et al., "Tumorigenicity of Simanian virus 40-Hepatocyte cel lines: Effect of in vitro and in vivo passage on expression of liver-specific genes and oncogenes," Molecular Cell Biol; vol. 8, pp. 4492-4501 (1988).

Wright and Duckett "Reawakening the cellular death program in neoplasia through the therapeutic blockade ofIAP function." J.Clin. Invest. vol. 115, pp. 2673-2678 (2005).

Xue et al., "Senescence and tumour clearance is triggered by p53 restoration in murine liver carcinomas," Nature, vol. 445, pp. 656-660 (Feb. 2007).

Yagi et al., "A WW domain-containing yes-associated protein (YAP) is a novel transcriptional co-activator," EMBO J. 18, 2551-2562 (1999).

Yang, et al., "A fluorescent orthotopic bone metastasis model of human prostate cancer" *Cancer Res.*, 59, (1999) pp. 781-786.

Yang, et al., "Genetically fluorescent melanoma bone and organ metastasis models" *Clin Cancer Res.*, 5 (1999) pp. 3549-3559.

Yang, et al., "Specific Double-Stranded RNA Interference in Undifferentiated Mouse Embryonic Stem Cells," Molecular and Cellular Biology, 21(22):7807-7816 (2001).

Yang, et al., "The transformation suppressor Pdcd4 is a novel eukaryotic translation initiation factor 4A binding protein that inhitibs translation" *Mol Cell Biol.*, 23, (2003) pp. 26-37.

Yang, et al., "Visualizing gene expression by whole-body fluorescence imaging" *Proc Natl. Acad. Sci. USA*, 97 (2000) pp. 12278-12282.

Yang, et al., "Whole-body optical imaging of green fluorescent protein-expressing tumors and metastases" *Proc. Natl. Acad. Sci. USA*, 97, (2000) pp. 1206-1211.

Yang, et al., "Widespread skeletal metastatic potential of human lung cancer revealed by green fluorescent protein expression" *Cancer Res.*, 58 (1998) pp. 4217-4221.

Yasui, K., et al. (2004). Alteration in numbers of genes as a mechanism for aCQuired drug resistance. Cancer Res. 64, 1403-1410.

Yu Q. et al., "Antisense inhibition of Chk2/hCds1 expression attenuates DNA damage-induced S and G2 checkpoints and enhances apoptotic activity in HEK 293 cells," Federation of European Biochemical Societies 505, 7-12 (2001).

Zender et al., "Representational oligonucleotide microarray (ROMA) identifies cIAP1/cIAP2 as candidate oncogenese in mouse and Human Hepatocarcinogenesis-validation of cIAP1 as a therapeutic target in liver cancer in a new mouse model of hepatocellular carcinoma," Hepatology, vol. 42, No. 4, Suppl 1, p. 244A (Oct. 2005).

Zeng et al., Use of RNA Polymerase II to Transcribe artificial MicroRNAS, Methods in Enzymology, 392:371-380 (2005).

Zhou et al., "An Rna polymerase II construct synthesizes short-hairpin RNA with a quantitative indicator and mediates highly efficient RNAi," Nucleic Acids Research, vol. 33(6) e62, pp. 1-8, (2005).

Zhou, B.B. and Bartek, J. (2004). Targeting the checkpoint kinases: chemosensitization versus chemoprotection. Nat. Rev. Cancer 4, 216-225.

* cited by examiner

SEQUENCE LISTING

<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tctaggcgcc ggaattagat ctctcg        26

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
cctgcaattg gatgcatggg gtcgtgc        27

<210> SEQ ID NO 3
<211> LENGTH: 25

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaattgaaga tctgggggat cgatc                                         25

<210> SEQ ID NO 4
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
catcaattgc tagaattctg gttgctcgag aggctggatc ggtcccggtg tcttc        55
```

METHODS FOR PRODUCING MICRORNAS

REFERENCE TO RELATED APPLICATION

This application is a division of U.S. Ser. No. 12/156,957, filed on Jun. 5, 2008, which is a continuation of U.S. Ser. No. 11/444,107, filed on May 31, 2006, which claims the benefit of the filing date of U.S. Provisional Application Ser. No. 60/686,135, entitled "METHODS FOR PRODUCING MICRORNAS," filed on May 31, 2005. The entire teachings of the above-referenced applications are incorporated herein by reference.

GOVERNMENT SUPPORT

Work described herein was funded, in whole or in part, by Mouse Models of Human Cancer Consortium Grant No. 25480211. The United States government has certain rights in the invention.

SEQUENCE LISTING

The instant application contains a Sequence Listing which was submitted electronically on Nov. 14, 2008, in parent application U.S. Ser. No. 12/156,957, and which is hereby incorporated by reference in its entirety.

BACKGROUND OF THE INVENTION

RNA interference (RNAi) has been used to silence the expression of a target gene. RNAi is a sequence-specific post-transcriptional gene silencing mechanism triggered by double-stranded RNA (dsRNA). It causes degradation of mRNAs homologous in sequence to the dsRNA. The mediators of the degradation are 21-23-nucleotide small interfering RNAs (siRNAs) generated by cleavage of longer dsRNAs (including hairpin RNAs) by DICER, a ribonuclease III-like protein. Molecules of siRNA typically have 2-3-nucleotide 3' overhanging ends resembling the RNAse III processing products of long dsRNAs that normally initiate RNAi. When introduced into a cell, they assemble an endonuclease complex (RNA-induced silencing complex), which then guides target mRNA cleavage. As a consequence of degradation of the targeted mRNA, cells with a specific phenotype of the suppression of the corresponding protein product are obtained (e.g., reduction of tumor size, metastasis, angiogenesis, and growth rates).

The small size of siRNAs, compared with traditional antisense molecules, prevents activation of the dsRNA-inducible interferon system present in mammalian cells. This helps avoid the nonspecific phenotypes normally produced by dsRNA larger than 30 base pairs in somatic cells. See, e.g., Elbashir et al., Methods 26:199-213 (2002); McManus and Sharp, Nature Reviews 3:737-747 (2002); Hannon, Nature 418:244-251 (2002); Brummelkamp et al., Science 296:550-553 (2002); Tuschl, Nature Biotechnology 20:446-448 (2002); U.S. Application US2002/0086356

SUMMARY OF THE INVENTION

One aspect of the invention provides an artificial nucleic acid construct comprising an RNA Polymerase II (Pol II) promoter operably linked to a coding sequence for expressing a precursor molecule for an siRNA, the siRNA inhibiting the expression of a target gene, wherein the nucleic acid construct directs the expression of the precursor molecule and/or the siRNA, and substantially inhibits the expression of the target gene when the artificial nucleic acid construct is stably integrated into a host cell genome.

In certain embodiments, the Pol II promoter is an inducible promoter, a tissue-specific promoter, or a developmental stage-specific promoter. For example, the inducible promoter may be a tetracyclin-responsive promoter, including commercially available TetON promoter (the transcription from which promoter is activated at the presence of tetracyclin (tet), doxycycline (Dox), or tet analog), or the TetOFF promoter (the transcription from which promoter is turned off at the presence of tetracyclin (tet), doxycycline (Dox), or a tet analog), e.g., those from Clontech, Inc.

In other embodiments, the inducible promoter may be selected from: a promoter operably linked to a lac operator (LacO), a LoxP-stop-LoxP system promoter, or a GeneSwitch™ or T-REx™ system promoter (Invitrogen), or equivalents thereof with identical or substantially similar mechanisms.

In yet other embodiments, the Pol II promoter can be any art-recognized Pol II promoters, such as an LTR promoter or a CMV promoter.

In certain embodiments, the precursor molecule may be a precursor microRNA, such as an artificial miR comprising coding sequence for the siRNA for the target gene. For example, the miR may comprise a backbone design of microRNA-30 (miR-30). Alternatively, the miR may comprise a backbone design of miR-15a, -16, -19b, -20, -23a, -27b, -29a, -30b, -30c, -104, -132s, -181, -191, -223. See US 2005/0075492A1 (incorporated herein by reference).

In other embodiments, the precursor molecule may be a short hairpin RNA (shRNA).

The constructs of the instant invention is highly potent, and a single integrated, copy of the subject nucleic acid construct is sufficient for substantially inhibiting the expression of the target gene. "Substantially inhibiting" as used herein includes inhibiting at least about 20%, or about 30%, 40%, 50%, 60%, 70%, 80%, 90%, 95%, 99% or close to 100% of the expression or mRNA and/or protein of the target gene.

The constructs of the invention may further comprise an enhancer for the Pol II promoter.

The constructs of the invention may further comprise a reporter gene under the control of a second promoter, such as a luciferase, a fluorescent protein (e.g. GFP, RFP, YFP, BFP, etc.), or an enzyme, or any other art-recognized reporter whose physical presence and/or activity can be readily assessed using an art-recognized method.

In certain embodiments, the second promoter and the reporter gene can be downstream of (3'-to) the coding sequence for the precursor molecule. In other embodiments, the reporter gene is translated from an internal ribosomal entry site (IRES) between a second promoter and the reporter gene.

In other embodiments, the coding sequence for expressing the precursor molecule may be embedded or inserted into the 5'-UTR (5'-untranslated region), 3'-UTR, or an intron of the reporter gene.

The constructs of the invention may further comprise at least one selectable marker, such as puromycin, zeocin, hygromycin, or neomycin, etc.

The constructs of the invention may further comprise a Pol III promoter upstream of the coding sequence for expressing the precursor molecule.

The constructs of the invention can be used to inhibit the expression of a number of different target genes. In certain embodiments, the target gene is associated with a disease condition such as cancer or infectious disease. For example, the target gene may be over-expressed or abnormally active in the disease. In addition, the target gene may be an oncogene or an antagonist/inhibitor or dominant negative mutation of a tumor suppressor gene.

Another aspect of the invention provides a cell comprising any of the subject nucleic acid constructs.

In certain embodiments, the cell may be a mammalian cell.

In certain embodiments, the cell may be a tissue culture cell (e.g., a primary cell, or a cell from an established cell line), a cell in vivo, or a cell manipulated ex vivo.

If the Pol II promoter is an inducible promoter, the cell may further comprise an additional construct for expressing an activator or an inhibitor of the inducible promoter. For example, if the inducible promoter is a tet-responsive promoter, the additional construct may encode tTA or rtTA. If the inducible promoter is a LacO-responsive promoter, the additional construct may encode LacI. If the inducible promoter is a LoxP-stop-LoxP system promoter, the additional construct may encode a Cre recombinase, which may be under the transcriptional control of an inducible promoter, a developmental stage-specific promoter, or a tissue-specific promoter.

Another aspect of the invention provides a non-human mammal comprising any of the subject cells described above. In certain embodiments, the non-human mammal may be a chimeric mammal some of whose somatic or germ cells are subject cells as described above. Alternatively, the non-human mammal may be a transgenic mammal all of whose somatic or germ cells are subject cells described above.

Another aspect of the invention provides a method for making a subject chimeric non-human mammal as described above, comprising introducing a construct according to any of the subject nucleic acid constructs into an embryonic stem (ES) cell and generating a chimeric mammal from the ES cell.

Another aspect of the invention provides a method for making a subject transgenic non-human mammal described above, comprising mating a subject chimeric non-human mammal described above with another animal from the same species.

Another aspect of the invention provides a method for inhibiting the expression of a target gene of interest in a cell, comprising introducing a subject construct into the cell, wherein the siRNA molecule derived from the precursor molecule is specific for the target gene.

In certain embodiments, the method further comprises inhibiting at least one additional target gene(s) of interest in the cell by introducing at least one additional constructs according to any one of the subject nucleic acid constructs into the cell, wherein each of the siRNA molecules derived from the precursor molecules are specific for the additional target genes, respectively.

Another aspect of the invention provides a method for treating a gene-mediated disease, comprising introducing into an individual having the disease a construct according to any of the subject nucleic acid constructs, where the siRNA derived from the precursor molecule is specific for the gene mediating the disease.

Another aspect of the invention provides a method of validating a gene as a potential target for treating a disease, comprising: (1) introducing a construct according to any one of the subject nucleic acid constructs described herein into a cell associated with the disease, wherein the siRNA molecule derived from the precursor molecule is specific for the gene; (2) assessing the effect of inhibiting the expression of the gene on one or more disease-associated phenotype; wherein a positive effect on at least one disease-associated phenotype is indicative that the gene is a potential target for treating the disease.

In certain embodiments, the gene is over-expressed or abnormally active in disease cells or tissues. Alternatively, the gene may be downstream of and is activated by a second gene over-expressed or abnormally active in disease cells or tissues. In addition, the product of the gene antagonizes an suppressor of a second gene over-expressed or abnormally active in disease cells or tissues.

In certain embodiments, the cell may be a tissue culture cell, such as a primary cell isolated from diseased tissues, or from an established cell line derived from diseased tissues.

In other embodiments, the cell is within diseased tissues, and step (2) above comprises evaluating one or more symptoms of the disease.

In certain embodiments, the cell may be one from a transgenic animal, such as one comprising any of the subject nucleic acid constructs.

For example, in a transgenic animal with a transgene comprising any of the subject nucleic acid constructs, the transgene may encode a precursor molecule, which, upon processing, generates a siRNA specific for the candidate target gene. Preferably, the expression of the precursor molecule is inducible, reversible, and/or tissue-specific.

In certain embodiments, the method further comprises assessing the side effect, if any, of knocking down the expression of the target gene in one or more tissues/organs other than the diseased tissue, wherein the target gene is a valid target if the side effect, if any, is acceptable to a person of skill in the respective art (e.g., when validating a drug target, such side effects resulting from impairment of the target gene function in other tissues must be acceptable to a physician or veterinarian).

In certain embodiments, the expression of the gene may be inducibly inhibited by a subject construct, or inducibly activated by turning down the expression of a subject construct.

It is also contemplated that all embodiments of the invention, including those specifically described for different aspects of the invention, can be combined with any other embodiments of the invention as appropriate.

Other features and advantages of the invention will be apparent from the following detailed description and claims.

DETAILED DESCRIPTION OF THE INVENTION

I. Overview

Figure 1:
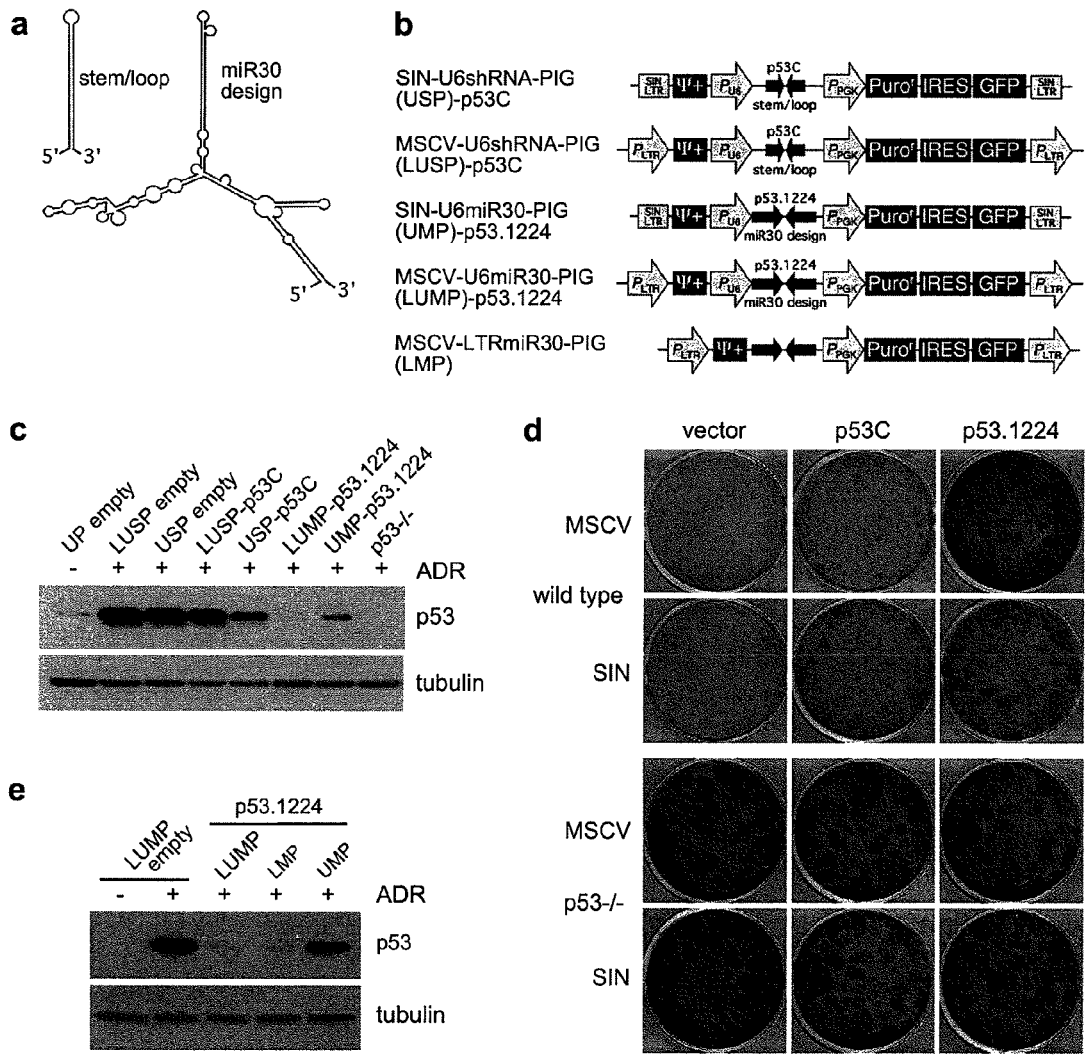
FIG. 1 shows effective knockdown via single copy expression of miR30-based shRNAs from a retroviral LTR promoter. (A) Schematic representation of predicted RNA folds for simple stem/loop and miR30 design shRNAs. Note extensive predicted folding for the ~300 nt pre-miR30 RNA. Folds were generated using mfold. (B) Retroviral vectors used to deliver shRNAs to mammalian cells. Provirus layouts are shown to indicate promoter activity of the integrated virus. Active promoters are shown as open arrows, with two inverted black arrows representing shRNA stem sequences. (C) Western blot analysis for p53 expression of NIH3T3 cells transduced with the retroviral vectors shown in B and selected in puromycin. A tubulin blot is shown as a loading control. (D) Colony formation assay for the cells shown in (C). Cells were seeded in 6 well plates at 2500 cells/well, and allowed to grow for 10 days before harvesting. (E) Western blot analysis for p53 expression in NIH3T3 cells transduced at less than 5% efficiency (assessed by GFP FACS; not shown) with the retroviral vectors shown in (B). A tubulin blot is shown as a loading control. Similar results were obtained in other cell types including wild type and p19ARF-null MEFs (data not shown).

RNA interference (RNAi) is normally triggered by double stranded RNA (dsRNA) or endogenous microRNA precursors (pre-miRNAs). Since its discovery, RNAi has emerged as a powerful genetic tool for suppressing gene expression in mammalian cells. Stable gene knockdown can be achieved by expression of synthetic short hairpin RNAs (shRNAs), traditionally from RNA polymerase III promoters.

The instant invention generally relates to the use of RNA Polymerase II promoters to express microRNA (miRNA) precursors and/or short hairpin RNAs (shRNAs), either in vitro, ex vivo, or in vivo, especially from as few as one single stably integrated expression construct. The single expression construct may be stably transfected/infected into a target cell, or may be a germline transgene. Transgenic animals with the subject RNAi constructs, which may be regulated to express mishRNA in an inducible, reversible, and/or tissue-specific manner, can be used to establish valuable animal models for certain disease, such as those associated with loss-of-function of certain target genes. The ability to control both the timing (e.g., at certain developmental stages) and location (e.g., tissue-specific) of target gene knock-down, including the ability to reverse the course of induction/inactivation, renders the subject system a powerful tool to study gene function and disease progression. Such animal models or cells thereof may also be used for drug screening or validation.

In certain embodiments, Pol II promoters controls the transcription of the subject miRNA/shRNA coding sequence. In general, any Pol II compatible promoters may be used for the instant invention.

In certain embodiments, various inducible Pol II promoters may be used to direct precursor miRNA/shRNA expression. Exemplary inducible Pol II promoters include the tightly regulatable Tet system (either TetOn or TetOFF), and a number of other inducible expression systems known in the art and/or described herein. The tet systems allows incremental and reversible induction of precursor miRNA/shRNA expression in vitro and in vivo, with no or minimal leakiness in precursor miRNA/shRNA expression. Such inducible system is advantages over the existing unidirectional Cre-lox strategies. Other systems of inducible expression may also be used with the instant constructs and methods.

In certain embodiments, expression of the subject miRNA/shRNA may be under the control of a tissue specific promoter, such as a promoter that is specific for: liver, pancreas (exocrine or endocrine portions), spleen, esophagus, stomach, large or small intestine, colon, GI tract, heart, lung, kidney, thymus, parathyroid, pineal glan, pituitary gland, mammary gland, salivary gland, ovary, uterus, cervix (e.g., neck portion), prostate, testis, germ cell, ear, eye, brain, retina, cerebellum, cerebrum, PNS or CNS, placenta, adrenal cortex or medulla, skin, lymph node, muscle, fat, bone, cartilage, synovium, bone marrow, epithelial, endothelial, vascular, nervous tissues, etc. The tissue specific promoter may also be specific for certain disease tissues, such as cancers. See Fukazawa et al., *Cancer Research* 64: 363-369, 2004 (incorporated herein by reference).

Any tissue specific promoters may be used in the instant invention. Merely to illustrate, Chen et al. (Nucleic Acid Research, Vol. 34, database issue, pages D104-D107, 2006) described TiProD, the Tissue-specific Promoter Database (incorporated herein by reference). Specifically, TiProD is a database of human promoter sequences for which some functional features are known. It allows a user to query individual promoters and the expression pattern they mediate, gene expression signatures of individual tissues, and to retrieve sets of promoters according to their tissue-specific activity or according to individual Gene Ontology terms the corresponding genes are assigned to. The database have defined a measure for tissue-specificity that allows the user to discriminate between ubiquitously and specifically expressed genes. The database is accessible at tiprod.cbi.pku dot edu.cn:8080/index.html. It covers most (if not all) the tissues described above.

In certain embodiments, if the reversibly inducible systems of the invention are used, the subject shRNAs are not designed to target the promoter regions of a target gene to avoid irreversible TGS.

In certain embodiments, artificial miRNA constructs based on, for example, miR30 (microRNA 30), may be used to express precursor miRNA/shRNA from single/low copy stable integration in cells in vivo, or through germline transmission in transgenic animals. For example, Silva et al. (Nature Genetics 37: 1281-88, 2005, incorporated herein by reference) have described extensive libraries of pri-miR-30-based retroviral expression vectors that can be used to down-regulate almost all known human (at least 28,000) and mouse (at least 25,000) genes (see RNAi Codex, a single database that curates publicly available RNAi resources, and provides the most complete access to this growing resource, allowing investigators to see not only released clones but also those that are soon to be released, available on the internet). Although such libraries are driven by Pol III promoters, they can be easily converted to the subject Pol II-driven promoters (see Methods in Dickins et al., Nat. Genetics 37: 1289-95, 2005; also see page 1284 in Silva et al., Nat. Genetics 37: 1281-89, 2005).

In certain embodiments, even a single copy of stably integrated precursor miRNA/shRNA construct results in effective knockdown of a target gene.

In certain embodiments, the inducible Tet system, coupled with the low-copy integration feature of invention, allows more flexible screening applications, such as in screening for potentially lethal shRNAs or synthetic lethal shRNAs.

In certain embodiments, the subject precursor miRNA cassette may be inserted within a gene encoded by the subject vector. For example, the subject precursor miRNA coding sequence may be inserted with an intron, the 5'- or 3'-UTR of a reporter gene such as GFP, etc.

In certain embodiments, cultured cells, such as wild type mouse fibroblasts or primary cells can be switched from proliferative to senescent states simply through regulated knockdown of p53 using the subject constructs and methods.

The constructs and methods of the invention is advantageous in several respects.

In one respect, stable precursor miRNA/shRNA expression may be effected through retroviral or lentiviral delivery of the miRNA/shRNAs, which is shown to be effective at single copy per cell. This allows very effective stable gene expression regulation at extremely low copy number per cell (e.g. one per cell), thus vastly advantageous over systems requiring the introduction of a large copy number of constructs into the target cell by, for example, transient transfection.

Compare to transfection where there are multiple copies (such as multiple episomal copies) of the shRNA construct, and the LTR is active, the instant system is preferable for stable expression of the shRNA.

Using the instant system, Applicants have discovered rapid and coordinated entry into senescence upon re-establishment of wild type p53 expression in p53 defective cells. Such an observation would not have been possible using previous technologies.

Another useful feature of the invention is that it is compatible with an established miR30 miRNA/shRNA library, which contains designed miRNA/shRNA constructs targeting almost all human and mouse genes. Any specific member of the library can be readily cloned (such as by PCR) into the vectors of the instant invention for Pol II-driven regulated and stable expression.

Other vector designs with different promoters have shown dependence on position of transcriptional start and stop sites. The subject method/system apparently has no such stringent requirements.

Applicants have also discovered that promoter interference between Pol II and Pol III promoters may prevent efficient transcription of encoded shRNA, while the use of miRNA precursor has largely overcome this problem.

Another aspect of the invention provides a method for drug target validation. The outcome of inhibiting the function of a gene, especially the associated effect in vivo, is usually hard to predict. Gene knock-out experiments offer valuable data for this purpose, but is expensive, time consuming, and potentially non-informative since many genes are required for normal development, such that loss-of-function mutation in such genes causes embryonic lethality. Using the methods of the instant invention, especially the inducible expression regulation system of the invention, any potential drug target/candidate gene for therapeutic intervention may be tested first by selectively up- and/or down-regulating their expression in vitro, ex vivo, or in vivo, and determining the effect of such regulated expression, especially in vivo effects on an organism. If disruption of the normal expression pattern of a candidate gene shows desired phenotypes in vitro and/or in vivo, the candidate gene is chosen as a target for therapeutic intervention. Various candidate compounds can then be screened to identify inhibitors or activators of such validated targets.

Another aspect of the invention provides a method to determine the effect of coordinated expression regulation of two or more genes. For example, miRNA/shRNA constructs for two more target genes may be introduced into a target cell (e.g., by stable integration) or an organism (e.g., by viral vector infection or transgenic techniques), and their expression may be individually or coordinately regulated using the inducible and/or tissue specific or developmental specific promoters according to the instant invention. Since different inducible promoters are available, the expression of the two or more target genes may be regulated either in the same or opposite direction (e.g., both up- or down-regulating, or one up one down, etc.). Such experiments can provide useful information regarding, inter alia, genetic interaction between related genes.

In certain embodiments, the instant invention allows highly efficient knockdown of a target gene from a single (retroviral) integration event, thus providing a highly efficient means for certain screening applications. For example, the instant system and methods may be used to test potentially lethal miRNA/shRNAs or synthetic lethal miRNA/shRNAs.

The invention also provide a method to treat certain cancer, especially those cancer overexpressing Ras pathway genes (e.g., Ras itself) and having impaired p53 function, comprising introducing into such cells an active p53 gene or gene product to induce senescence and/or apoptosis, thereby killing the cancer cells, or at least inhibit cancer progression and/or growth.

The general feature of the invention having been described, the following section provides certain illustrative aspects of the invention that may be combined in specific embodiments. Other similar or equivalent art-recognized methods may also be readily adapted for use in the instant invention.

II. MicroRNA and RNAi Design

DNA vectors that express perfect complementary short hairpins RNAs (shRNAs) are commonly used to generate functional siRNAs. However, the efficacy of gene silencing mediated by different short-hairpin derived siRNAs may be inconsistent, and a substantial number of short-hairpin siRNA expression vectors can trigger an anti-viral interferon response (*Nature Genetics* 34: 263, 2003). Moreover, siRNA short-hairpins are typically processed symmetrically, in that both the functional siRNA strand and its complement strand are incorporated into the RISC complex. Entry of both strands into the RISC can decrease the efficiency of the desired regulation and increase the number of off-target mRNAs that are influenced. In comparison, endogenous microRNA (miRNA) processing and maturation is a fairly efficient process that is not expected to trigger an anti-viral interferon response. This process involves sequential steps that are specified by the information contained in miRNA hairpin and its flanking sequences.

MicroRNAs (miRNAs) are endogenously encoded ~22-nt-long RNAs that are generally expressed in a highly tissue- or developmental-stage-specific fashion and that post-transcriptionally regulate target genes. More than 200 distinct miRNAs having been identified in plants and animals, these small regulatory RNAs are believed to serve important biological functions by two prevailing modes of action: (1) by repressing the translation of target mRNAs, and (2) through RNA interference (RNAi), that is, cleavage and degradation of mRNAs. In the latter case, miRNAs function analogously to small interfering RNAs (siRNAs). Importantly, miRNAs are expressed in a highly tissue-specific or developmentally regulated manner and this regulation is likely key to their predicted roles in eukaryotic development and differentiation. Analysis of the normal role of miRNAs will be facilitated by techniques that allow the regulated over-expression or inappropriate expression of authentic miRNAs in vivo, whereas the ability to regulate the expression of siRNAs will greatly increase their utility both in cultured cells and in vivo. Thus one can design and express artificial microRNAs based on the features of existing microRNA genes, such as the gene encoding the human miR-30 microRNA. These miR30-based shRNAs have complex folds, and, compared with simpler stem/loop style shRNAs, are more potent at inhibiting gene expression in transient assays.

miRNAs are first transcribed as part of a long, largely single-stranded primary transcript (Lee et al., *EMBO J.* 21: 4663-4670, 2002). This primary miRNA transcript is generally, and possibly invariably, synthesized by RNA polymerase II (pol II) and therefore is normally polyadenylated and may be spliced. It contains an ~80-nt hairpin structure that encodes the mature ~22-nt miRNA as part of one arm of the stem. In animal cells, this primary transcript is cleaved by a nuclear RNaseIII-type enzyme called Drosha (Lee et al., *Nature* 425: 415-419, 2003) to liberate a hairpin miRNA precursor, or pre-miRNA, of ~65 nt, which is then exported to the cytoplasm by exportin-5 and the GTP-bound form of the Ran cofactor (Yi et al., *Genes Dev.* 17: 3011-3016, 2003). Once in the cytoplasm, the pre-miRNA is further processed by Dicer, another RNaseIII enzyme, to produce a duplex of ~22 bp that is structurally identical to an siRNA duplex (Hutvagner et al., *Science* 293: 834-838, 2001). The binding of protein components of the RNA-induced silencing complex (RISC), or RISC cofactors, to the duplex results in incorporation of the mature, single-stranded miRNA into a RISC or RISC-like protein complex, whereas the other strand of the duplex is degraded (Bartel, *Cell* 116: 281-297, 2004).

The miR-30 architecture can be used to express miRNAs or siRNAs from pol II promoter-based expression plasmids. See also Zeng et al., *Methods in Enzymology* 392: 371-380, 2005 (incorporated herein by reference).

Figure 2:
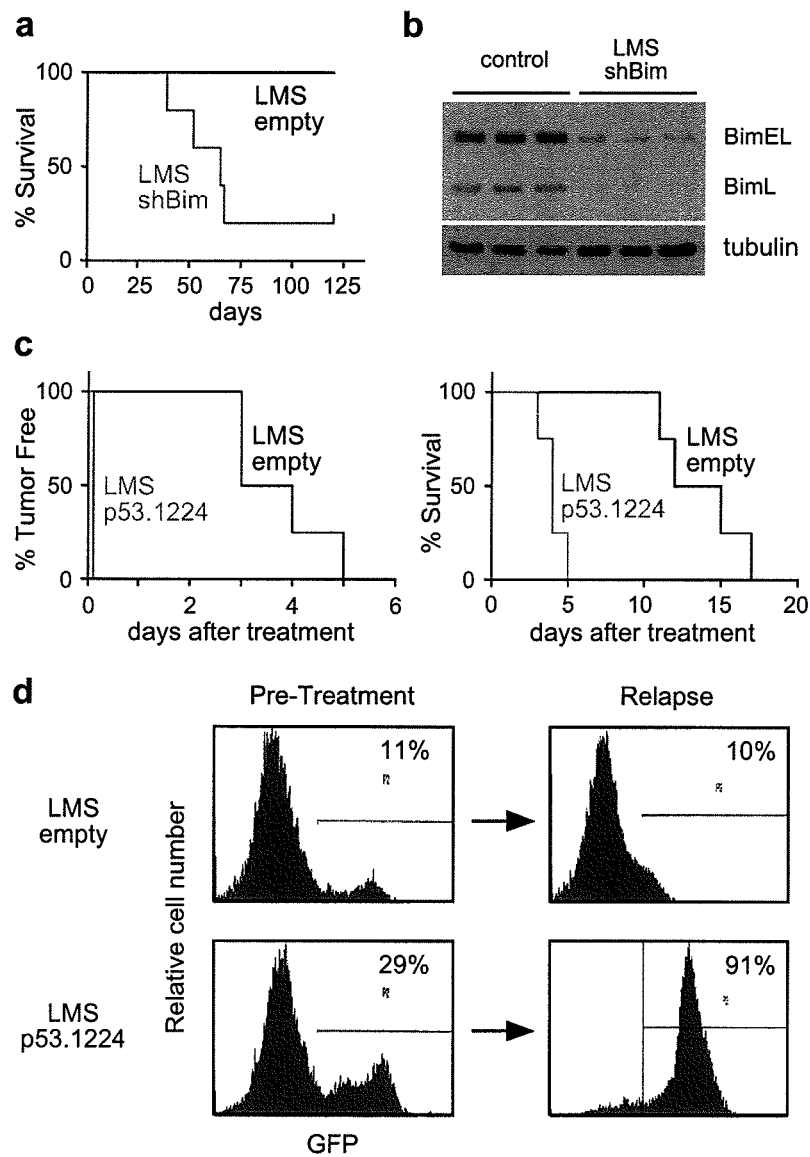
FIG. 2 shows that RNA polymerase II-driven shRNAs can effectively promote tumorigenesis and chemotherapy resistance in vivo. (A) Kaplan-Meier curve showing mouse survival following adoptive transfer of Eµ-Myc HSCs infected with LTR-driven Bim shRNAs. (B) Western blot showing reduced BimEL and BimL expression in Eµ-Myc lymphomas expressing Bim shRNAs. Control: archived tumors arising from Eµ-Myc HSCs (on either a wild type, ARF$^{+/-}$ or p53$^{+/-}$ background; not shown) were used as controls for Bim expression. (C) Kaplan-Meier curves showing tumor-free survival (left) and overall survival (right) for mice harboring p19ARF-null lymphomas infected with either the LMP-p53.1224 retrovirus or vector control. Tumor-bearing mice were given a single 10 mg/kg dose of adriamycin at day zero. (D) Flow cytometry analysis of GFP expression in lymphoma cells harvested from the mice in (A). Representative histograms show the percent of GFP-positive cells at the time of treatment (left) and after tumor relapse (right).

FIG. 2B of Zeng (supra) shows the predicted secondary structure of the miR-30 precursor hairpin ("the miR-30 cassette"). Boxed are extra nucleotides that were added originally for subcloning purposes (Zeng and Cullen, *RNA* 9: 112-123, 2003; Zeng et al., *Mol. Cell.* 9: 1327-1333, 2002). They represent XhoI-BglII sites at the 50 end and BamHI-XhoI sites at the 30 end. These appended nucleotides extend the minimal miR-30 precursor stem shown by several basepairs, similar to the in vivo situation where the primary miR-30 precursor is transcribed from its genomic locus (Lee et al., *Nature* 425: 415-419, 2003), and an extended stem of at least 5 bp is essential for efficient miR-30 production. Based on the numbering in FIG. 2B, mature miR-30 is encoded by nucleotides 44 to 65 and anti-miR-30 by nucleotides 3 to 25 of this precursor. In the simplest expression setting, the cytomegalovirus (CMV) immediate early enhancer/promoter may be used to transcribe the miR-30 cassette. The cassette is preceded by a leader sequence of approximately 100 nt and followed by approximately 170 nt before the polyadenylation site (Zeng et al., *Mol. Cell.* 9: 1327-1333, 2002). These lengths are arbitrary and can be longer or shorter. Mature 22-nt miR-30 can be made from such constructs.

Several other authentic miRNAs have been over-expressed by using analogous RNA pol II-based expression vectors or even pol III-dependent promoters (Chen et al., *Science* 303: 83-86, 2004; Zeng and Cullen, *RNA* 9: 112-123, 2003). Expression simply requires the insertion of the entire predicted miRNA precursor stem-loop structure into the expression vector at an arbitrary location. Because the actual extent of the precursor stem loop can sometimes be difficult to accurately predict, it is generally appropriate to include ~50 bp of flanking sequence on each side of the predicted ~80-nt miRNA stem-loop precursor to be sure that all cis-acting sequences necessary for accurate and efficient Drosha processing are included (Chen et al., *Science* 303: 83-86, 2004).

In an exemplary embodiment, to make the miR-30 expression cassette, the sequence from +1 to 65 (excluding the 15-nt terminal loop of the miR-30 cassette, FIG. 2B of Zeng) may be replaced as follows: the sequence from nucleotides 39 to 61, which is perfectly complementary to a target gene sequence, will act as the active strand during RNAi. The sequence from nucleotides 2 to 23 is thus designed to preserve the double-stranded stem in the miR-30-target cassette, but nucleotide +1 is now a C, to create a mismatch with nucleotide 61, a U, just like nucleotides 1 and 65 in the miR-30 cassette (FIG. 2B). Because the 30 arm of the stem (miR-30-target) is the active component for RNAi, changes in the 50 arm of the stem will not affect RNAi specificity. A 2-nt bulge may be present in the stem region of the authentic miR-30 precursor (FIG. 2B of Zeng). A break in the helical nature of the RNA stem may help ward off nonspecific effects, such as induction of an interferon response (Bridge et al., *Nat. Genet.* 34: 263-264, 2003) in expressing cells. This may be why miRNA precursors almost invariably contain bulges in the predicted stem. The miR-30 cassette in FIG. 2A of Zeng is then substituted with the miR-30-target cassette, and the resulting expression plasmid can be transfected into target cells.

The use of pol II promoters, especially when coupled with an inducible expression system (such as the TetOFF system of Clontech) offers flexibility in regulating the production of miRNAs in cultured cells or in vivo. Selection of stable cell lines leads to less leaky expression in the absence of the activator or presence of doxycycline, and therefore a stronger induction.

In certain embodiments, it would be advantageous if the antisense strand, for example, of the above miR-30-target construct is preferentially made as a mature miRNA, because its opposite strand does not have any known target. The relative basepairing stability at the 50 ends of an siRNA duplex is a strong determinant of which strand will be incorporated into RISC and hence be active in RNAi; the strand whose 50 end has a weaker hydrogen bonding pattern is preferentially incorporated into RISC, the RNAi effecter complex (Khvorova et al., *Cell* 115: 209-216, 2003; Schwarz et al., *Cell* 115: 208-299, 2003). This same principle can also be applied to the design of DNA vector-based siRNA expression strategies, including the one described here. However, for artificial miRNAs, the fact that the internal cleavage sites by Drosha and Dicer cannot be precisely predicted at present adds a degree of uncertainty as a 1- or 2-nt shift in the cleavage site can generate rather different hydrogen bonding patterns at the 50 ends of the resulting duplex, thus changing which strand of the duplex intermediate is incorporated into RISC. This is in contrast to the situation with synthetic siRNA duplexes, which have defined ends. On the other hand, any minor heterogeneity at the ends of an artificial miRNA duplex intermediate might not be a problem, as the miRNAs would still be perfectly complementary to their target.

The role of internal loop, stem length, and the surrounding sequences on the expression of miRNAs from miR-30-derived cassettes may also be systematically examined to optimize expression of the miR-based smRNA. Such analyses may suggest design elements that would maximize the yield of the intended RNA products. On the other hand, some heterogeneity could be inevitable. In addition to the 50-end rule, specific residues at some positions within an siRNA may also enhance siRNA function (Reynolds et al., *Nat. Biotech.* 22: 326-330, 2004).

In general, picking a target region with more than 50% AU content and designing a weak 50 end base pair on the antisense strand would be a good starting point in the design of any artificial miRNA/siRNA expression plasmid (Khvorova et al., *Cell* 115: 209-216, 2003; Reynolds et al., *Nat. Biotech.* 22: 326-330, 2004; Schwarz et al., *Cell* 115: 208-299, 2003).

In certain embodiments, expression of the miR-30 cassette may be in the antisense orientation, especially when the cassette is to be used in lentiviral or retroviral vectors. This is partly because miRNA processing may result in the degradation of the remainder of the primary miRNA transcript.

In other embodiments, vectors may contain inserts expressing more than one miRNAs. In such constructs, the fact that each miRNA stem-loop precursor is independently excised from the primary transcript by Drosha cleavage to give rise to a pre-miRNA allows simultaneous expression of several artificial or authentic miRNAs by a tandem array on a precursor RNA transcript.

Genome wide libraries of shRNAs based on the miR30 precursor RNA have also been generated. Each member of such libraries target specific human or mouse genes, and may be readily converted to the vectors/expression systems of the instant invention. The following section describes the design of such libraries.

Paddison et al. (*Nature Methods* 1(2): 163-67, 2004, incorporated herein by reference) have described a genome-wise library of shRNAs based on the miR30 precursor RNA, which may be adapted for use in the instant invention. The described vector pSHAG-MAGIC2 (pSM2) is roughly equivalent to pSHAG-MAGIC1 as described in Paddison et al. *Methods*

*Mol. Biol.* 265: 85-100 (2004), incorporated herein by reference. The few notable exceptions include: the new cloning strategy is based on the use of a single oligonucleotide that contains the hairpin and common 5' and 3' ends as a PCR template (see FIG. 2 of Paddison, *Nature Methods* 1(2): 163-67, 2004). The resulting PCR product is then cloned into the hairpin cloning site of the pSM2 vector, which drives miR-30-styled hairpins by the human U6 promoter. Inserts from this library may be excised (see Example below) and cloned into the instant vectors for Pol II-driven expression of the same miR-30-styled hairpins. This allows the instant methods to be coupled with the existing library of miR-30-style constructs that contains most human and mouse genes.

Paddison also describes the detailed methods for designing 22-nucleotide sequences (targeting a target gene) that can be inserted into the precursor miRNA, PCR protocols for amplification, and relevant critical steps and trouble-shootings, etc. (all incorporated herein by reference).

MicroRNAs (including the siRNA products and artificial microRNAs as well as endogenous microRNAs) have potential for use as therapeutics as well as research tools, e.g. analyzing gene function. As a general method, the mature microRNA (miR) of the invention, especially those non-miR-30 based microRNA constructs of the invention may also be produced according to the following description.

In certain embodiments, the methods for efficient expression of microRNA involve the use of a precursor microRNA molecule having a microRNA sequence in the context of microRNA flanking sequences. The precursor microRNA is composed of any type of nucleic acid based molecule capable of accommodating the microRNA flanking sequences and the microRNA sequence. Examples of precursor microRNAs and the individual components of the precursor (flanking sequences and microRNA sequence) are provided herein. The invention, however, is not limited to the examples provided. The invention is based, at least in part, on the discovery of an important component of precursor microRNAs, that is, the microRNA flanking sequences. The nucleotide sequence of the precursor and its components may vary widely.

In one aspect a precursor microRNA molecule is an isolated nucleic acid including microRNA flanking sequences and having a stem-loop structure with a microRNA sequence incorporated therein. An "isolated molecule" is a molecule that is free of other substances with which it is ordinarily found in nature or in vivo systems to an extent practical and appropriate for its intended use. In particular, the molecular species are sufficiently free from other biological constituents of host cells or if they are expressed in host cells they are free of the form or context in which they are ordinarily found in nature. For instance, a nucleic acid encoding a precursor microRNA having homologous microRNA sequences and flanking sequences may ordinarily be found in a host cell in the context of the host cell genomic DNA. An isolated nucleic acid encoding a microRNA precursor may be delivered to a host cell, but is not found in the same context of the host genomic DNA as the natural system. Alternatively, an isolated nucleic acid is removed from the host cell or present in a host cell that does not ordinarily have such a nucleic acid sequence. Because an isolated molecular species of the invention may be admixed with a pharmaceutically-acceptable carrier in a pharmaceutical preparation or delivered to a host cell, the molecular species may comprise only a small percentage by weight of the preparation or cell. The molecular species is nonetheless isolated in that it has been substantially separated from the substances with which it may be associated in living systems.

An "isolated precursor microRNA molecule" is one which is produced from a vector having a nucleic acid encoding the precursor microRNA. Thus, the precursor microRNA produced from the vector may be in a host cell or removed from a host cell. The isolated precursor microRNA may be found within a host cell that is capable of expressing the same precursor. It is nonetheless isolated in that it is produced from a vector and, thus, is present in the cell in a greater amount than would ordinarily be expressed in such a cell.

The term "nucleic acid" is used to mean multiple nucleotides (i.e. molecules comprising a sugar (e.g. ribose or deoxyribose) linked to a phosphate group and to an exchangeable organic base, which is either a substituted pyrimidine (e.g. cytosine (C), thymidine (T) or uracil (U)) or a substituted purine (e.g. adenine (A) or guanine (G)). The term shall also include polynucleosides (i.e. a polynucleotide minus the phosphate) and any other organic base containing polymer. Purines and pyrimidines include but are not limited to adenine, cytosine, guanine, thymidine, inosine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. Other such modifications are well known to those of skill in the art. Thus, the term nucleic acid also encompasses nucleic acids with substitutions or modifications, such as in the bases and/or sugars.

"MicroRNA flanking sequence" as used herein refers to nucleotide sequences including microRNA processing elements. MicroRNA processing elements are the minimal nucleic acid sequences which contribute to the production of mature microRNA from precursor microRNA. Often these elements are located within a 40 nucleotide sequence that flanks a microRNA stem-loop structure. In some instances the microRNA processing elements are found within a stretch of nucleotide sequences of between 5 and 4,000 nucleotides in length that flank a microRNA stem-loop structure.

Thus, in some embodiments the flanking sequences are 5-4,000 nucleotides in length. As a result, the length of the precursor molecule may be, in some instances at least about 150 nucleotides or 270 nucleotides in length. The total length of the precursor molecule, however, may be greater or less than these values. In other embodiments the minimal length of the microRNA flanking sequence is 10, 20, 30, 40, 50, 60, 70, 80, 90, 100, 150, 200 and any integer there between. In other embodiments the maximal length of the microRNA flanking sequence is 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900 4,000 and any integer there between.

The microRNA flanking sequences may be native microRNA flanking sequences or artificial microRNA flanking sequences. A native microRNA flanking sequence is a nucleotide sequence that is ordinarily associated in naturally existing systems with microRNA sequences, i.e., these sequences are found within the genomic sequences surrounding the minimal microRNA hairpin in vivo. Artificial microRNA flanking sequences are nucleotides sequences that are not found to be flanking to microRNA sequences in naturally existing systems. The artificial microRNA flanking sequences may be flanking sequences found naturally in the context of other microRNA sequences. Alternatively they may be composed of minimal microRNA processing elements which are found within naturally occurring flanking sequences and inserted into other random nucleic acid sequences that do not naturally occur as flanking sequences or only partially occur as natural flanking sequences.

The microRNA flanking sequences within the precursor microRNA molecule may flank one or both sides of the stem-loop structure encompassing the microRNA sequence. Thus, one end (i.e., 5') of the stem-loop structure may be adjacent to a single flanking sequence and the other end (i.e., 3') of the stem-loop structure may not be adjacent to a flanking sequence. Preferred structures have flanking sequences on both ends of the stem-loop structure. The flanking sequences may be directly adjacent to one or both ends of the stem-loop structure or may be connected to the stem-loop structure through a linker, additional nucleotides or other molecules.

A "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and the term is used consistently with its known meaning in the art. The actual primary sequence of nucleotides within the stem-loop structure is not critical to the practice of the invention as long as the secondary structure is present. As is known in the art, the secondary structure does not require exact base-pairing. Thus, the stem may include one or more base mismatches. Alternatively, the base-pairing may be exact, i.e. not include any mismatches.

In some instances the precursor microRNA molecule may include more than one stem-loop structure. The multiple stem-loop structures may be linked to one another through a linker, such as, for example, a nucleic acid linker or by a microRNA flanking sequence or other molecule or some combination thereof.

In an alternative embodiment, useful interfering RNAs can be designed with a number of software programs, e.g., the OligoEngine siRNA design tool available at wwv.olioengine.com. The siRNAs of this invention may range about, e.g., 19-29 basepairs in length for the double-stranded portion. In some embodiments, the siRNAs are hairpin RNAs having an about 19-29 bp stem and an about 4-34 nucleotide loop. Preferred siRNAs are highly specific for a region of the target gene and may comprise any about 19-29 bp fragment of a target gene mRNA that has at least one, preferably at least two or three, by mismatch with a nontarget gene-related sequence. In some embodiments, the preferred siRNAs do not bind to RNAs having more than 3 mismatches with the target region.

III. Expression Vectors and Host Cells

The invention also includes vectors for producing precursor microRNA molecules. Generally these vectors include a sequence encoding a precursor microRNA and (in vivo) expression elements. The expression elements include at least one promoter, such as a Pol II promoter, which may direct the expression of the operably linked microRNA precursor (e.g. the shRNA encoding sequence). The vector or primary transcript is first processed to produce the stem-loop precursor molecule. The stem-loop precursor is then processed to produce the mature microRNA.

RNA polymerase III (Pol III) transcription units normally encode the small nuclear RNA U6 (see Tran et al., *BMC Biotechnology* 3: 21, 2003, incorporate herein by reference), or the human RNAse P RNA Hi. However, RNA polymerase II (Pol II) transcription units (e.g., units containing a CMV promoter) is preferred for use with inducible expression. It will be appreciated that in the vectors of the invention, the subject shRNA encoding sequence may be operably linked to a variety of other promoters.

In some embodiments, the promoter is a type II tRNA promoter such as the tRNAVa promoter and the tRNAmet promoter. These promoters may also be modified to increase promoter activity. In addition, enhancers can be placed near the promoter to enhance promoter activity. Pol II enhancer may also be used for Pol III promoters. For example, an enhancer from the CMV promoter can be placed near the U6 promoter to enhance U6 promoter activity (Xia et al., *Nuc Acids Res* 31, 2003).

In certain embodiments, the subject Pol II promoters are inducible promoters. Exemplary inducible Pol II systems are available from Invitrogen, e.g., the GeneSwitch™ or T-REx™ systems; from Clontech (Palo Alto, Calif.), e.g., the TetON and TetOFF systems.

An exemplary Tet-responsive promoter is described in WO 04/056964A2 (incorporated herein by reference). See, for example, FIG. 1 of WO 04/056964A2. In one construct, a Tet operator sequence (TetOp) is inserted into the promoter region of the vector. TetOp is preferably inserted between the PSE and the transcription initiation site, upstream or downstream from the TATA box. In some embodiments, the TetOp is immediately adjacent to the TATA box. The expression of the subject shRNA encoding sequence is thus under the control of tetracycline (or its derivative doxycycline, or any other tetracycline analogue). Addition of tetracycline or Dox relieves repression of the promoter by a tetracycline repressor that the host cells are also engineered to express.

In the TetOFF system, a different tet transactivator protein is expressed in the tetOFF host cell. The difference is that Tet/Dox, when bind to an activator protein, is now required for transcriptional activation. Thus such host cells expressing the activator will only activate the transcription of an shRNA encoding sequence from a TetOFF promoter at the presence of Tet or Dox.

An alternative inducible promoter is a lac operator system, as illustrated in FIG. 2A of WO 04/056964 A2 (incorporated by reference). Briefly, a Lac operator sequence (LacO) is inserted into the promoter region. The LacO is preferably inserted between the PSE and the transcription initiation site, upstream or downstream of the TATA box. In some embodiments, the LacO is immediately adjacent to the TATA box. The expression of the RNAi molecule (shRNA encoding sequence) is thus under the control of IPTG (or any analogue thereof). Addition of IPTG relieves repression of the promoter by a Lac repressor (i.e., the LacI protein) that the host cells are also engineered to express. Since the Lac repressor is derived from bacteria, its coding sequence may be optionally modified to adapt to the codon usage by mammalian transcriptional systems and to prevent methylation. In some embodiments, the host cells comprise (i) a first expression construct containing a gene encoding a Lac repressor operably linked to a first promoter, such as any tissue or cell type specific promoter or any general promoter, and (ii) a second expression construct containing the dsRNA-coding sequence operably linked to a second promoter that is regulated by the Lac repressor and IPTG. Administration of IPTG results in expression of dsRNA in a manner dictated by the tissue specificity of the first promoter.

Yet another inducible system, a LoxP-stop-LoxP system, is illustrated in FIGS. 3A-3E of WO 04/056964 A2 (incorporated by reference). The RNAi vector of this system contains a LoxP-Stop-LoxP cassette before the hairpin or within the loop of the hairpin. Any suitable stop sequence for the promoter can be used in the cassette. One version of the LoxP Stop-LoxP system for Pol II is described in, e.g., Wagner et al., *Nucleic Acids Research* 25:4323-4330, 1997. The "Stop" sequences (such as the one described in Wagner, sierra, or a run of five or more T nucleotides) in the cassette prevent the RNA polymerase III from extending an RNA transcript beyond the cassette. Upon introduction of a Cre recombinase, however, the LoxP sites in the cassette recombine, removing the Stop sequences and leaving a single LoxP site. Removal of the Stop sequences allows transcription to proceed through the hairpin sequence, producing a transcript that can be efficiently processed into an open-ended, interfering dsRNA. Thus, expression of the RNAi molecule is induced by addition of Cre.

In some embodiments, the host cells contain a Cre-encoding transgene under the control of a constitutive, tissue-specific promoter. As a result, the interfering RNA can only be inducibly expressed in a tissue-specific manner dictated by that promoter. Tissue-specific promoters that can be used include, without limitation: a tyrosinase promoter or a TRP2 promoter in the case of melanoma cells and melanocytes; an MMTV or WAP promoter in the case of breast cells and/or cancers; a Villin or FABP promoter in the case of intestinal cells and/or cancers; a RIP promoter in the case of pancreatic beta cells; a Keratin promoter in the case of keratinocytes; a Probasin promoter in the case of prostatic epithelium; a Nestin or GFAP promoter in the case of CNS cells and/or cancers; a Tyrosine Hydroxylase, S100 promoter or neurofilament promoter in the case of neurons; the pancreas-specific promoter described in Edlund et al., *Science* 230: 912-916, 1985; a Clara cell secretory protein promoter in the case of lung cancer; and an Alpha myosin promoter in the case of cardiac cells.

Cre expression also can be controlled in a temporal manner, e.g., by using an inducible promoter, or a promoter that is temporally restricted during development such as Pax3 or Protein O (neural crest), Hoxal (floorplate and notochord), Hoxb6 (extraembryonic mesoderm, lateral plate and limb mesoderm and midbrain-hindbrain junction), Nestin (neuronal lineage), GFAP (astrocyte lineage), Lck (immature thymocytes). Temporal control also can be achieved by using an inducible form of Cre. For example, one can use a small molecule controllable Cre fusion, for example a fusion of the Cre protein and the estrogen receptor (ER) or with the progesterone receptor (PR). Tamoxifen or RU486 allow the Cre-ER or Cre-PR fusion, respectively, to enter the nucleus and recombine the LoxP sites, removing the LoxP Stop cassette. Mutated versions of either receptor may also be used. For example, a mutant Cre-PR fusion protein may bind RU486 but not progesterone. Other exemplary Cre fusions are a fusion of the Cre protein and the glucocorticoid receptor (GR). Natural GR ligands include corticosterone, cortisol, and aldosterone. Mutant versions of the GR receptor, which respond to, e.g., dexamethasone, triamcinolone acetonide, and/or RU38486, may also be fused to the Cre protein.

In certain embodiments, additional transcription units may be present 3' to the shRNA portion. For example, an internal ribosomal entry site (IRES) may be positioned downstream of the shRNA insert, the transcription of which is under the control of a second promoter, such as the PGK promoter. The IRES sequence may be used to direct the expression of a operably linked second gene, such as a reporter gene (e.g., a fluorescent protein such as GFP, BFP, YFP, etc., an enzyme such as luciferase (Promega), etc.). The reporter gene may serve as an indication of infection/transfection, and the efficiency and/or amount of mRNA transcription of the shRNA-IRES-reporter cassette/insert. Optionally, one or more selectable markers (such as puromycin resistance gene, neomycin resistance gene, hygromycin resistance gene, zeocin resistance gene, etc.) may also be present on the same vector, and are under the transcriptional control of the second promoter. Such markers may be useful for selecting stable integration of the vector into a host cell genome.

Certain exemplary vectors useful for expressing the precursor microRNAs are shown in the examples. Thus the invention encompasses the nucleotide sequence of such vectors as well as variants thereof.

In general, variants typically will share at least 40% nucleotide identity with any of the described vectors, in some instances, will share at least 50% nucleotide identity; and in still other instances, will share at least 60% nucleotide identity. The preferred variants have at least 70% sequence homology. More preferably the preferred variants have at least 80% and, most preferably, at least 90% sequence homology to the described sequences.

Variants with high percentage sequence homology can be identified, for example, using stringent hybridization conditions. The term "stringent conditions", as used herein, refers to parameters with which the art is familiar. More specifically, stringent conditions, as used herein, refer to hybridization at 65° C. in hybridization buffer (3.5×SSC, 0.02% Ficoll, 0.02% polyvinyl pyrolidone, 0.02% bovine serum albumin, 2.5 mM $NaH_2PO_4$ (pH 7), 0.5% SDS, 2 mM EDTA). SSC is 0.15M sodium chloride/0.15M sodium citrate, pH 7; SDS is sodium dodecyl sulphate; and EDTA is ethylenediaminetetraacetic acid. After hybridization, the membrane to which the DNA is transferred is washed at 2×SSC at room temperature and then at 0.1×SSC/0.1×SDS at 65° C. There are other conditions, reagents, and so forth which can be used, which result in a similar degree of stringency. Such variants may be further subject to functional testing such that variants that substantially preserve the desired/relevant function of the original vectors are selected/identified.

The "in vivo expression elements" are any regulatory nucleotide sequence, such as a promoter sequence or promoter-enhancer combination, which facilitates the efficient expression of the nucleic acid to produce the precursor microRNA. The in vivo expression element may, for example, be a mammalian or viral promoter, such as a constitutive or inducible promoter or a tissue specific promoter. Constitutive mammalian promoters include, but are not limited to, polymerase II promoters as well as the promoters for the following genes: hypoxanthine phosphoribosyl transferase (HPTR), adenosine deaminase, pyruvate kinase, and β-actin. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as in vivo expression element of the invention also include inducible promoters. Inducible promoters are expressed in the presence of an inducing agent. For example, the metallothionein promoter is induced to promote transcription in the presence of certain metal ions. Other inducible promoters are known to those of ordinary skill in the art.

One useful inducible expression system that can be adapted for use in the instant invention is the Tet-responsive system, including both the TetON and TetOFF embodiments.

TetOn system is a commercially available inducible expression system from Clontech Inc. This is of particular interest because current siRNA expression systems utilize pol III promoters, which are difficult to adapt for inducible expression. The Clontech TetON system includes the pRev-TRE vector, which can be packaged into retrovirus and used to infect a Tet-On cell line expressing the reverse tetracycline-controlled transactivator (rtTA). Once introduced into the TetON host cell, the shRNA insert can then be inducibly expressed in response to varying concentrations of the tetracycline derivate doxycycline (Dox).

In general, the in vivo expression element shall include, as necessary, 5' non-transcribing and 5' non-translating sequences involved with the initiation of transcription. They optionally include enhancer sequences or upstream activator sequences as desired.

Vectors include, but are not limited to, plasmids, phagemids, viruses, other vehicles derived from viral or bacterial sources that have been manipulated by the insertion or incorporation of the nucleic acid sequences for producing the precursor microRNA, and free nucleic acid fragments which can be attached to these nucleic acid sequences. Viral and retroviral vectors are a preferred type of vector and include, but are not limited to, nucleic acid sequences from the following viruses: retroviruses, such as: Moloney murine leukemia virus; Murine stem cell virus, Harvey murine sarcoma virus; murine mammary tumor virus; Rous sarcoma virus; adenovirus; adeno-associated virus; SV40-type viruses; polyoma viruses; Epstein-Barr viruses; papilloma viruses; herpes viruses; vaccinia viruses; polio viruses; lentiviruses; and RNA viruses such as any retrovirus. One can readily employ other unnamed vectors known in the art.

Viral vectors are generally based on non-cytopathic eukaryotic viruses in which non-essential genes have been replaced with the nucleic acid sequence of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Genetically altered retroviral expression vectors have general utility for the high-efficiency transduction of nucleic acids in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "*Methods in Molecular Biology*," vol. 7, Humana Press, Inc., Cliffton, N.J. (1991).

Exemplary vectors are disclosed herein and in US 2005/0075492 A2 (incorporated herein by reference) and WO 04/056964 A2 (incorporated herein by reference).

The invention also encompasses host cells transfected with the subject vectors, especially host cell lines with stably integrated shRNA constructs. In certain embodiments, the subject host cell contains only a single copy of the integrated construct expressing the desired shRNA (optionally under the control of an inducible and/or tissue specific promoter). Host cells include for instance, cells (such as primary cells) and cell lines, e.g. prokaryotic (e.g., *E. coli*), and eukaryotic (e.g., dendritic cells, CHO cells, COS cells, yeast expression systems and recombinant baculovirus expression in insect cells, etc.). Exemplary cells include: NIH3T3 cells, MEFs, 293 or 293T cells, CHO cells, hematopoietic stem/progenitor cells, cancer cells, etc.

IV. Methods of Using

In certain aspects, methods of the invention comprise contacting and introducing into a target cell with a subject vector capable of expressing a precursor microRNA as described herein, to regulate the expression of a target gene in the cell. The vector produces the microRNA transcript, which is then processed into precursor microRNA in the cell, which is then processed to produce the mature functional microRNA which is capable of altering accumulation of a target protein in the target cell. Accumulation of the protein may be effected in a number of different ways. For instance the microRNA may directly or indirectly affect translation or may result in cleavage of the mRNA transcript or even effect stability of the protein being translated from the target mRNA. MicroRNA may function through a number of different mechanisms. The methods and products of the invention are not limited to any one mechanism. The method may be performed in vitro, e.g., for studying gene function, ex vivo or in vivo, e.g. for therapeutic purposes.

An "ex vivo" method as used herein is a method which involves isolation of a cell from a subject, manipulation of the cell outside of the body, and reimplantation of the manipulated cell into the subject. The ex vivo procedure may be used on autologous or heterologous cells, but is preferably used on autologous cells. In preferred embodiments, the ex vivo method is performed on cells that are isolated from bodily fluids such as peripheral blood or bone marrow, but may be isolated from any source of cells. When returned to the subject, the manipulated cell will be programmed for cell death or division, depending on the treatment to which it was exposed. Ex vivo manipulation of cells has been described in several references in the art, including Engleman, E. G., 1997, Cytotechnology, 25:1; Van Schooten, W., et al., 1997, Molecular Medicine Today, June, 255; Steinman, R. M., 1996, Experimental Hematology, 24, 849; and Gluckman, J. C., 1997, Cytokines, Cellular and Molecular Therapy, 3:187. The ex vivo activation of cells of the invention may be performed by routine ex vivo manipulation steps known in the art. In vivo methods are also well known in the art. The invention thus is useful for therapeutic purposes and also is useful for research purposes such as testing in animal or in vitro models of medical, physiological or metabolic pathways or conditions.

The ex vivo and in vivo methods are performed on a subject. A "subject" shall mean a human or non-human mammal, including but not limited to, a dog, cat, horse, cow, pig, sheep, goat, primate, rat, and mouse, etc.

In some instances the mature microRNA is expressed at a level sufficient to cause at least a 2-fold, or in some instances, a 10 fold reduction in accumulation of the target protein. The level of accumulation of a target protein may be assessed using routine methods known to those of skill in the art. For instance, protein may be isolated from a target cell and quantitated using Western blot analysis or other comparable methodologies, optionally in comparison to a control. Protein levels may also be assessed using reporter systems or fluorescently labeled antibodies. In other embodiments, the mature microRNA is expressed at a level sufficient to cause at least a 2, 5, 15, 20, 25, 30, 35, 40, 45, 50, 55, 60, 65, 70, 75, or 100 fold reduction in accumulation of the target protein. The "fold reduction" may be assessed using any parameter for assessing a quantitative value of protein expression. For instance, a quantitative value can be determined using a label i.e. fluorescent, radioactive linked to an antibody. The value is a relative value that is compared to a control or a known value.

Different microRNA sequences have different levels of expression of mature microRNA and thus have different effects on target mRNA and/or protein expression. For instance, in some cases a microRNA may be expressed at a high level and may be very efficient such that the accumulation of the target protein is completely or near completely blocked. In other instances the accumulation of the target protein may be only reduced slightly over the level that would ordinarily be expressed in that cell at that time under those conditions in the absence of the mature microRNA. Complete inhibition of the accumulation of the target protein is not essential, for example, for therapeutic purposes. In many cases partial or low inhibition of accumulation may produce a preferred phenotype. The actual amount that is useful will depend on the particular cell type, the stage of differentiation, conditions to which the cell is exposed, the modulation of other target proteins, etc.

The microRNAs may be used to knock down gene expression in vertebrate cells for gene-function studies, including target-validation studies during the development of new pharmaceuticals, as well as the development of human disease models and therapies, and ultimately, human gene therapies.

The methods of the invention are useful for treating any type of "disease", "disorder" or "condition" in which it is desirable to reduce the expression or accumulation of a particular target protein(s). Diseases include, for instance, but are not limited to, cancer, infectious disease, cystic fibrosis, blood disorders, including leukemia and lymphoma, spinal muscular dystrophy, early-onset Parkinsonism (Waisman syndrome) and X-linked mental retardation (MRX3).

Cancers include but are not limited to biliary tract cancer; bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS-associated leukemias and adult T-cell leukemia lymphoma; intraepithelial neoplasms including Bowen's disease and Paget's disease; liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilms tumor.

An infectious disease, as used herein, is a disease arising from the presence of a foreign microorganism in the body. A microbial antigen, as used herein, is an antigen of a microorganism. Microorganisms include but are not limited to, infectious virus, infectious bacteria, and infectious fungi.

Examples of infectious virus include but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Examples of infectious bacteria include but are not limited to: *Helicobacter pyloris, Borelia burgdorferi, Legionella pneumophilia, Mycobacteria* sps (e.g. *M. tuberculosis, M. avium, M. intracellulare, M kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter sp., Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia*, and *Actinomyces israelli.*

Examples of infectious fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium* such as *Plasmodium falciparum, Plasmodium malariae, Plasmodium ovale*, and *Plasmodium vivax* and *Toxoplasma gondii*.

The vectors of this invention can be delivered into host cells via a variety of methods, including but not limited to, liposome fusion (transposomes), infection by viral vectors, and routine nucleic acid transfection methods such as electroporation, calcium phosphate precipitation and microinjection. In some embodiments, the vectors are integrated into the genome of a transgenic animal (e.g., a mouse, a rabbit, a hamster, or a nonhuman primate). Diseased or disease-prone cells containing these vectors can be used as a model system to study the development, maintenance, or progression of a disease that is affected by the presence or absence of the interfering RNA.

Expression of the miRNA/siRNA introduced into a target cell may be confirmed by art-recognized techniques; such as Northern blotting using a nucleic acid probe. For cell lines that are more difficult to transfect, more extracted RNA can be used for analyses, optionally coupled with exposing the film longer. Once expression of the miRNA/siRNA is confirmed, the DNA construct can then be tested for RNAi efficacy against a cotransfected construct encoding the target protein or directly against an endogenous target. In the latter case, one preferably should have a clear idea of transfection efficiency and of the half-life of the target protein before performing the experiment.

V. Pharmaceutical Use and Methods of Administration

In one aspect, the invention provides a method of administering any of the compositions described herein to a subject. When administered, the compositions are applied in a therapeutically effective, pharmaceutically acceptable amount as a pharmaceutically acceptable formulation. As used herein, the term "pharmaceutically acceptable" is given its ordinary meaning. Pharmaceutically acceptable compounds are generally compatible with other materials of the formulation and are not generally deleterious to the subject. Any of the compositions of the present invention may be administered to the subject in a therapeutically effective dose. A "therapeutically effective" or an "effective" as used herein means that amount necessary to delay the onset of, inhibit the progression of, halt altogether the onset or progression of, diagnose a particular condition being treated, or otherwise achieve a medically desirable result, i.e., that amount which is capable of at least partially preventing, reversing, reducing, decreasing, ameliorating, or otherwise suppressing the particular condition being treated. A therapeutically effective amount can be determined on an individual basis and will be based, at least in part, on consideration of the species of mammal, the mammal's age, sex, size, and health; the compound and/or composition used, the type of delivery system used; the time of administration relative to the severity of the disease; and whether a single, multiple, or controlled-release dose regiment is employed. A therapeutically effective amount can be determined by one of ordinary skill in the art employing such factors and using no more than routine experimentation.

The terms "treat," "treated," "treating," and the like, when used herein, refer to administration of the systems and methods of the invention to a subject, which may, for example, increase the resistance of the subject to development or further development of cancers, to administration of the composition in order to eliminate or at least control a cancer or a infectious disease, and/or to reduce the severity of the cancer or infectious disease, or symptoms thereof. Such terms also include prevention of disease/condition in, for example, subjects/individuals predisposed to such diseases/conditions, or at high risk of developing such diseases/conditions.

When administered to a subject, effective amounts will depend on the particular condition being treated and the desired outcome. A therapeutically effective dose may be determined by those of ordinary skill in the art, for instance, employing factors such as those further described below and using no more than routine experimentation.

In administering the systems and methods of the invention to a subject, dosing amounts, dosing schedules, routes of administration, and the like may be selected so as to affect known activities of these systems and methods. Dosage may be adjusted appropriately to achieve desired drug levels, local or systemic, depending upon the mode of administration. The doses may be given in one or several administrations per day. As one example, if daily doses are required, daily doses may be from about 0.01 mg/kg/day to about 1000 mg/kg/day, and in some embodiments, from about 0.1 to about 100 mg/kg/day or from about 1 mg/kg/day to about 10 mg/kg/day. Parental administration, in some cases, may be from one to several orders of magnitude lower dose per day, as compared to oral doses. For example, the dosage of an active compound when parentally administered may be between about 0.1 micrograms/kg/day to about 10 mg/kg/day, and in some embodiments, from about 1 microgram/kg/day to about 1 mg/kg/day or from about 0.01 mg/kg/day to about 0.1 mg/kg/day.

In some embodiments, the concentration of the active compound(s), if administered systemically, is at a dose of about 1.0 mg to about 2000 mg for an adult of 70 kg body weight, per day. In other embodiments, the dose is about 10 mg to about 1000 mg/70 kg/day. In yet other embodiments, the dose is about 100 mg to about 500 mg/70 kg/day. Preferably, the concentration, if applied topically, is about 0.1 mg to about 500 mg/gm of ointment or other base, more preferably about 1.0 mg to about 100 mg/gm of base, and most preferably, about 30 mg to about 70 mg/gm of base. The specific concentration partially depends upon the particular composition used, as some are more effective than others. The dosage concentration of the composition actually administered is dependent at least in part upon the particular physiological response being treated, the final concentration of composition that is desired at the site of action, the method of administration, the efficacy of the particular composition, the longevity of the particular composition, and the timing of administration relative to the severity of the disease. Preferably, the dosage form is such that it does not substantially deleteriously affect the mammal. The dosage can be determined by one of ordinary skill in the art employing such factors and using no more than routine experimentation.

In the event that the response of a particular subject is insufficient at such doses, even higher doses (or effectively higher doses by a different, more localized delivery route) may be employed to the extent that subject tolerance permits. Multiple doses per day are also contemplated in some cases to achieve appropriate systemic levels within the subject or within the active site of the subject. In some cases, dosing amounts, dosing schedules, routes of administration, and the like may be selected as described herein, whereby therapeutically effective levels for the treatment of cancer are provided.

In certain embodiments where cancers are being treated, a composition of the invention may be administered to a subject who has a family history of cancer, or to a subject who has a genetic predisposition for cancer. In other embodiments, the composition is administered to a subject who has reached a particular age, or to a subject more likely to get cancer. In yet other embodiments, the compositions is administered to subjects who exhibit symptoms of cancer (e.g., early or advanced). In still other embodiments, the composition may be administered to a subject as a preventive measure. In some embodiments, the inventive composition may be administered to a subject based on demographics or epidemiological studies, or to a subject in a particular field or career.

Administration of a composition of the invention to a subject may be accomplished by any medically acceptable method which allows the composition to reach its target. The particular mode selected will depend of course, upon factors such as those previously described, for example, the particular composition, the severity of the state of the subject being treated, the dosage required for therapeutic efficacy, etc. As used herein, a "medically acceptable" mode of treatment is a mode able to produce effective levels of the active compound(s) of the composition within the subject without causing clinically unacceptable adverse effects.

Any medically acceptable method may be used to administer a composition to the subject. The administration may be localized (i.e., to a particular region, physiological system, tissue, organ, or cell type) or systemic, depending on the condition being treated. For example, the composition may be administered orally, vaginally, rectally, buccally, pulmonary, topically, nasally, transdermally, through parenteral injection or implantation, via surgical administration, or any other method of administration where suitable access to a target is achieved. Examples of parenteral modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be preferred in some embodiments because of the convenience to the subject as well as the dosing schedule. Compositions suitable for oral administration may be presented as discrete units such as hard or soft capsules, pills, cachettes, tablets, troches, or lozenges, each containing a predetermined amount of the active compound. Other oral compositions suitable for use with the invention include solutions or suspensions in aqueous or non-aqueous liquids such as a syrup, an elixir, or an emulsion. In another set of embodiments, the composition may be used to fortify a food or a beverage.

Injections can be e.g., intravenous, intradermal, subcutaneous, intramuscular, or interperitoneal. The composition can be injected interdermally for treatment or prevention of infectious disease, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

In general, the compositions of the invention may be delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. Examples of non-biodegradable polymers include ethylene vinyl acetate, poly(meth)acrylic acid, polyamides, copolymers and mixtures thereof.

Bioadhesive polymers of particular interest include bioerodible hydrogels described by H. S. Sawhney, C. P. Pathak and J. A. Hubell in Macromolecules, (1993) 26:581-587, the teachings of which are incorporated herein, polyhyaluronic acids, casein, gelatin, glutin, polyanhydrides, polyacrylic acids, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In certain embodiments of the invention, the administration of the composition of the invention may be designed so as to result in sequential exposures to the composition over a certain time period, for example, hours, days, weeks, months or years. This may be accomplished, for example, by repeated administrations of a composition of the invention by one of the methods described above, or by a sustained or controlled release delivery system in which the composition is delivered over a prolonged period without repeated administrations. Administration of the composition using such a delivery system may be, for example, by oral dosage forms, bolus injections, transdermal patches or subcutaneous implants. Maintaining a substantially constant concentration of the composition may be preferred in some cases.

Other delivery systems suitable for use with the present invention include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing drugs are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the composition is contained in a form within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system may be used to deliver one or more embodiments of the invention.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments of the invention. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

In some embodiments, the compositions of the invention may include pharmaceutically acceptable carriers with formulation ingredients such as salts, carriers, buffering agents', emulsifiers, diluents, excipients, chelating agents, fillers, drying agents, antioxidants, antimicrobials, preservatives, binding agents, bulking agents, silicas, solubilizers, or stabilizers that may be used with the active compound. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa. Those of skill in the art can readily determine the various parameters for preparing and formulating the compositions of the invention without resort to undue experimentation.

In some embodiments, the present invention includes the step of forming a composition of the invention by bringing an active compound into association or contact with a suitable carrier, which may constitute one or more accessory ingredients. The final compositions may be prepared by any suitable technique, for example, by uniformly and intimately bringing the composition into association with a liquid carrier, a finely divided solid carrier or both, optionally with one or more formulation ingredients as previously described, and then, if necessary, shaping the product.

In some embodiments, the compositions of the present invention may be present as pharmaceutically acceptable salts. The term "pharmaceutically acceptable salts" includes salts of the composition, prepared in combination with, for example, acids or bases, depending on the particular compounds found within the composition and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable acids include amino acids such as arginate, aspartate, glutamate, and the like.

The invention also includes methods for quantitating a level of precursor microRNA expression. The method involves incorporating a precursor microRNA into a reporter system, transfecting a host cell with the reporter system, and detecting expression of a reporter gene product to quantitate the level of precursor microRNA expression. In some embodiments the reporter system includes a firefly luciferase reporter gene.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

VI. Exemplary Uses

Drug Target Validation

Good drugs are potent and specific; that is, ideally, they must have strong effects on a specific biological pathway or tissue (such as the disease tissue), while having minimal effects on all other pathways or all other tissues (e.g., healthy tissues). Confirmation that a compound inhibits the intended target (drug target validation) and the identification of undesirable secondary effects are among the main challenges in developing new drugs.

Modern drug screening typically requires tremendous amounts of time and financial resources. Ideally, before even committing to such an extensive drug development program to identify a drug, one would like to know whether the intended drug target would even make a good target for treating a disease. That is, whether antagonizing the function of the intended target (such as a disease-associated oncogene or survival gene), would be sufficient/effective to treat the disease, and whether such treatment would bear an acceptable risk or side effect. For example, if a cancer is determined to be caused by an activating mutation in the Ras pathway, or caused by abnormal activity of a survival gene such as Bcl-2, the subject system can be used to generate animal models for drug target validation. Specifically, one can generate a transgenic mouse with the subject tet-responsive mishRNA expression, with the mishRNA targeting a gene that is a potential drug target (i.e., Ras or Bcl-2 in this example). Tumors with various initiating lesions can then be made in the mouse, and the mishRNA can be switched on in the tumor (if, for example, a tet-ON regulator is used). Such mishRNA expression mimics the action of a (yet to be identified) drug that would interfere with that target. If knocking down the target gene is effective to reverse or stall the course of the disease, the target gene is a valid target.

Optionally, the mishRNA transgene can be switched on in a number of tissues or organs, or even in the whole organism, in order to verify the potential side effects of the (yet to be identified) drug on other healthy tissues/organs.

Thus another aspect of the invention provides an animal useful for drug target validation, comprising a germline transgene encompassing the subject artificial nucleic acid, which transcription is driven by a Pol II promoter. The expression of the encoded precursor molecule (such as one based on the miR30-design) leads to an siRNA that targets a candidate drug target. Optionally, the precursor molecule is expressed in an inducible, reversible, and/or tissue-specific manner.

In a related aspect, the invention provides a method for drug target validation, comprising antagonizing the function of a candidate drug target (gene) using a subject cell or animal (e.g., a transgenic animal) encompassing the subject artificial nucleic acid, either in vitro or in vivo, and assessing the ability of the encoded precursor molecule to reverse or stall the disease progress or a particular phenotype associated with a pathological condition. Optionally, the method further comprises assessing any side effects of inhibiting the function of the target gene on one or more healthy organs/tissues.

Animal Disease Model

The subject nucleic acid constructs enables one to switch on or off a target gene or certain target genes (e.g., by using crossing different lines of transgenic animals to generate multiple-transgenic animals) inducibly, reversibly, and/or in a tissue-specific manner. This would faciliate conditional knock-out or turning-on of any target gene(s) in a tissue-specific manner, and/or during a specific developmental stage (e.g., embryonic, fetal, neonatal, postnatal, adult, etc.). Animals bearing such transgenes may be treated, such as by providing a tet analog in drinking water, to turn on or off certain genes to allow certain diseases to develop/manifest. Such system and methods are particularly useful, for example, to analize the role of any known or suspected tumor suppressor genes in the maintenance of immortalized or transformed states, and in continued tumor growth in vivo.

In certain embodiments, the extent of gene knock-down may be controlled to achieve a desired level of gene expression. Such animals or cell (healthy or diseased) may be used to study disease progress, response to certain treatment, and/or screening for drug leads.

The ability of the subject system to use a single genomic copy of the Pol II promoter-driven mishRNA cassette to control gene expression is particularly valuable for complex library screening.

The subject gene knock-down by expression of shRNA-mirs may be very similar to overexpression of protein-coding cDNAs. Thus any expression systems allowing targeted, regulated and tissue-specific expression, which have traditionally be limited to gene overexpression studies, may now be adapted for loss-of-function studies, especially when combined with the available genome-wide, sequence-verified banks of miR-30-based shRNAs targeting model organisms, such as human and mouse.

EXAMPLES

The invention now being generally described, it will be more readily understood by reference to the following examples, which are included merely for purposes of illustration of certain aspects and embodiments of the present invention, and are not intended to limit the invention.

Introduction

In contrast to RNA Polymerase II promoters which are used by genes encoding proteins, RNA Polymerase III (Pol III) promoters, such as U6 and H1 promoters, normally drive the transcription of several endogenous small nuclear RNAs (snRNAs). For this reason, Pol III promoters have been widely adopted to drive transcription of synthetic short hairpin RNAs (shRNAs) in cells and animals. Applicants and others have used shRNAs driven by U6 promoters to achieve stable knockdown of target genes. Delivery of Pol III promoter-shRNA cassettes by retroviral transduction of mammalian cells results in stable suppression of target gene expression.

However, shRNA driven by Pol III promoters has certain practical problems. First of all, unlike Pol II promoters, the Pol III promoters do not lend themselves to regulation. Secondly, such Pol III-driven shRNAs can be ineffective inhibitors of their target mRNAs when expressed from a single-copy vector.

Here, Applicants have used certain RNA Polymerase II (Pol II) expression systems to allow potent and regulatable RNAi in mammalian cells. Applicants have shown that miR30 design shRNAs expressed from the LTR promoter of an integrated retrovirus suppress target genes more effectively than when expressed from an RNA polymerase III promoter, even when expressed from a single-copy in the genome (e.g., from a stably transfected or a transgenic copy). Furthermore, regulated shRNA expression was also achieved by using inducible/reservible Pol II promoters, such as a Tet-responsive Pol II promoter.

Example I

RNA Polymerase III Promoters are Sufficient for Stable shRNA Expression

In order to identify a preferred retroviral vector for delivery of promoter-shRNA cassettes into mammalian cells, Applicants compared two vectors based on the murine stem cell virus (MSCV) and the self-inactivating (SIN) retroviral vector, respectively. The 5'-long terminal repeat (5'-LTR) promoter of the SIN provirus is transcriptionally inactive, thus using the SIN 5'-UTR promoter in this construct (e.g., USP-p53C, see below) serves as a control for the construct using the functional MSCV Pol II promoter (e.g., LUSP-p53C, see below).

Into each vector, Applicants cloned the U6 RNA polymerase III promoter upstream of a sequence encoding p53C, a short hairpin RNA (shRNA) that targets murine p53. The shRNA p53C is predicted to fold into a simple, symmetrical shRNA with a 29-nucleotide stem and an eight nt loop (FIG. 1A, left). Also in each vector, a puroR-IRES-GFP (PIG) cassette under the control of the PGK promoter was operably linked downstream of the U6-shRNA cassette (FIG. 1B).

Primary murine embryonic fibroblasts (MEFs) were infected with either the SIN-U6shRNA-PIG (UP)-p53C construct (USP-p53C), the MSCV-U6shRNA-PIG (LUP)-p53C construct (LUSP-p53C), or a control virus, and subject to puromycin selection to establish stably-infected cell lines.

After treatment with the DNA-damaging agent adriamycin to induce p53 expression, cells stably-integrated by the above constructs were harvested, and their p53 expression levels were assessed by Western blotting. Interestingly, Applicants found that p53 knockdown was far more effective in cells transduced with the SIN retrovirus (FIG. 1C), indicating that the internal U6 Pol III promoter is sufficient for expression of the p53C shRNA in mammalian cells (since the SIN Pol II promoter is inactive in the USP-p53C construct). Also surprisingly, our observations suggest that transcription from the upstream MSCV LTR promoter, a strong RNA polymerase II promoter, inhibited shRNA function and p53 knockdown in this context. This effect may be due to promoter interference between the LTR Pol II and U6 Pol III promoters.

Similar results were obtained for several other shRNAs with simple stem/loop folds similar to p53C (data not shown), verifying the general applicability of using RNA polymerase III promoters alone for expression of this style (the simple stem-loop style) of shRNA.

Example II

LTR Pol II Promoter is More Effective than RNA Polymerase III Promoter in Directing Integrated miR30-Design shRNAs Suppression of Target Genes This example demonstrates that synthetic shRNAs with folds designed to mimic endogenous microRNA (miRNA) precursors can effectively inhibit target gene expression. To illustrate, Applicants used the exemplary miR30-design shRNAs (designated microRNA-based shRNAs, or mishRNAs) to demonstrate stable suppression of gene expression in mammalian cells, which strategy can be generally applied to other microRNA (miRNA) precursors. Specifically, Applicants recovered a mishRNA referred to as p53.1224 (so named because the predicted siRNA begins at nucleotide 1224 of the p53 cDNA) from the mishRNA library (a genome wide miR30-based shRNA library).

As shown above, standard stem-loop shRNAs are most effectively expressed from RNA polymerase III (Pol III) promoters such as the U6 promoter. Applicants sub-cloned a U6 promoter-p53.1224 cassette into a murine stem cell virus (MSCV) and a self-inactivating (SIN) retroviral vector, thus generating two vectors designed to express miR-based shRNAs (as opposed to the stem-loop shRNA): MSCV/LTR-U6miR30-PIG (LUMP)-p53.1224 and SIN-U6miR30-PIG (UMP)-p53.1224 (FIG. 1B). One difference between the mishRNA and the standard stem-loop shRNA is that the miR30 precursor RNA is approximately 300 nt in length and is predicted to fold into an extensive secondary structure (FIG. 1A, right).

Applicants have previously constructed similar vectors expressing a standard stem-loop shRNA targeting p53 (p53C), producing MSCV/LTR-U6shRNA-PIG (LUSP)-p53C or SIN-U6shRNA-PIG (USP)-p53C (see above and FIG. 1B). All four constructs were introduced into early passage murine embryonic fibroblasts (MEFs). The resulting cell populations were assessed for p53 knockdown after adriamycin treatment (a DNA damaging agent that stabilizes p53), and the ability to form colonies when plated at low density (a functional readout of p53 loss).

Contrast to what was observed for the simple stem-loop shRNA, the MSCV-based p53.1224 mishRNA (LUMP-p53.1224) driven by a functional Pol II promoter was more effective at suppressing p53 than its SIN-based counterpart (UMP-p53.1224) devoid of a functional Pol II promoter, producing nearly undetectable p53 levels as assessed by immunoblotting (FIG. 1C, compare lanes 6, 7, and 8). As shown above, for the standard stem-loop shRNA, the SIN-based p53C shRNA (USP-p53C) was more effective at suppressing p53 than its MSCV-derived counterpart (LUSP-p53C), verifying that the U6 promoter is sufficient for stem/loop shRNA expression (FIG. 1C). The ability of each vector to suppress p53 correlated precisely with its ability to stimulate colony formation at low density, with cells expressing the MSCV-based p53.1224 vector producing as many colonies as p53-null cells (FIG. 1D).

Southern blotting using a GFP probe verified that these differences were not due to variation in retroviral copy number (data nor shown).

This vector preference was also observed for several other mishRNAs and stem-loop shRNAs targeting diverse gene products (data not shown). Thus, in general, mishRNAs can be remarkably potent when stably expressed from retroviral vectors, particularly those with a functional 5'-LTR (with a Pol II promoter). In the examples shown herein, this system achieved near-complete (if not complete) target gene knockdown.

Example III

Pol II Promoter Contributes to Functional shRNA Production

The more potent knockdown produced by mishRNAs expressed from the MSCV vector compared with the SIN vector implies that the 5'-LTR contributes to optimal mishRNA expression. To determine whether the 5'-LTR promoter, a strong Pol II promoter, is sufficient for effective gene knockdown using mishRNAs, Applicants introduced the p53.1224 shRNA into an MSCV vector lacking a U6 promoter (MSCV/LTRmiR30-PIG (LMP) (FIG. 1B). To facilitate comparison, Applicants introduced this vector and its LUMP and UMP counterparts into NIH3T3 cells at a low multiplicity of infection (<5% efficiency) such that the vast majority of transduced cells should contain single proviral integrations. Remarkably, both vectors harboring the MSCV LTR (LUMP-p53.1224 and LMP-p53.1224) suppressed p53 expression extremely efficiently, and were far superior to UMP-p53.1224, which expresses p53.1224 from the U6 promoter alone (FIG. 1E). Similar results were obtained in other cell types including wild type and p19ARF-null MEFs (data not shown).

Thus, transcription of mishRNAs from Pol II promoters (such as the retroviral LTR in this example) is sufficient for highly effective target gene knockdown, even when expressed at single copy, and even in the absence of any Pol III promoters. Such features are extremely valuable for knockdown screens using complex libraries, where infected cells are unlikely to contain multiple copies of a given shRNA vector.

The fact that the 5'-LTR Pol II promoter produced results similar to those of the 5'-LTR+U6 promoters (Pol II and Pol III promoters), suggested that in this case, U6 may be mainly acting as a "spacer." As the combined effects of the 5'-LTR and U6 promoters appeared to be more effective than U6 alone, promoter interference is unlikely, and rather, it suggests dominance of the LTR promoter.

Interestingly, GFP is less abundant in cells with LTR-miR30 transcript. While not wishing to be bound by any particular theory, this is likely due to degradation of this transcript after nuclear processing by Drosha. Since microRNA clusters, much GFP appeared to be translated from the IRES on the long LTR transcript.

Example IV

In Vivo Loss-of-Function Phenotypes can be Recapitulated Using miR30-Design shRNAs Expressed from Pol II Promoters Stable expression of stem/loop shRNAs can produce loss of function phenotypes in mice. To determine whether miR30-derived shRNAs expressed from poi II promoters can efficiently modulate gene expression in vivo, Applicants targeted genes for which the null phenotype was known. For example, inactivation of the BH3-only protein Bim (a pro-apoptotic member of the Bcl-2 family) accelerates lymphomagenesis in Eμ-myc transgenic mice. To this end, Applicants have demonstrated that miR30-design shRNAs targeting Bim would also cooperate with myc during lymphomagenesis. Indeed, mice reconstituted with Eμ-myc hematopoetic stem cells (HSCs) transduced with two independent miR30-design shRNAs targeting Bim (collectively referred to as shBim, and expressed from the LTR of MSCV/LTRmiR30-SV40-GFP (LMS), a derivative of LMP that lacks a Pol III promoter) formed tumors much more rapidly than animals reconstituted with stem cells expressing a control vector (FIG. 2A, P<0.05). Importantly, lymphomas arising in animals transduced with shBim were GFP-positive, expressed low levels of Bim (FIG. 2B), and displayed a mature (IgM+) B cell phenotype uniquely characteristic of Bim null lymphomas (data not shown). Thus, in vivo loss of function phenotypes can be recapitulated using miR30-design shRNAs expressed from Pol II promoters.

Example V

Identification and Characterization of Genes that Modify Drug Responses In Vivo siRNAs have been used to identify modulators of drug action, but are not suitable for long-term assays or in vivo systems. The miR30-based vectors described above enable the identification and characterization of genes that modify drug responses in vivo.

As an illustrative example, Applicants examined the ability of a miR30-design p53 shRNA to promote chemoresistance in Eμ-myc lymphomas, which respond poorly to therapy in the absence of p53. Applicants introduced LMS-p53.1224 (co-expressing GFP) into chemosensitive Eμ-myc lymphoma cells at ~10% infection efficiency and transplanted the mixed cell populations into syngeneic recipient mice. Upon lymphoma manifestation, animals were treated with the chemotherapeutic drug adriamycin and monitored for tumor response. Strikingly, mice harboring lymphomas expressing LMS-p53.1224 did not regress following adriamycin treatment and showed significantly reduced overall survival relative to control tumor-bearing mice (FIG. 2C). This indicates that the LMS-p53.1224 construct effectively knocked-down p53 expression in tumor cells, resulting in their poor response (or chemoresistance) to therapy. Furthermore, the percentage of GFP positive cells dramatically increased in lymphomas harboring p53.1224 but not the control vector, indicating a selective advantage for p53.1224 expressing cells (FIG. 2D).

These results demonstrated that sufficient p53 knockdown may promote in vivo chemoresistance. Such an animal mode (or tumor cells therein) may also be used to screen (in vivo or in vitro) for compounds that can overcome chemoresistance in p53 negative cells.

Together, these data indicate that mishRNAs expressed from Pol II promoters are suitable for a variety of in vivo applications, with strong potential for transgenic animals, tissue specific gene knockdowns and in vivo forward genetic screens.

Example VI

Pol II Promoter-Driven Inducible and Reversible shRNA Production from Low-Copy Stable Integration RNAi inhibits gene function without altering DNA sequence, therefore its effects are potentially reversible. Given our findings that low copy Pol II promoters can effectively drive mishRNAs from a single integrated construct, Applicants adapted the traditional inducible protein expression systems, such as the tetracycline (tet)-regulated Pol II promoter TRE-CMV, to achieve inducible stable expression of mishRNAs.

Many inducible promoters are known in the art in the context of protein expression. These inducible systems can all be adapted to express the mishRNAs of the subject invention. In one illustrative example, the TRE-CMV promoter consists of a tandem array of tet transactivator binding sites fused to a minimal CMV promoter. Transactivator protein tTA transactivates the TRE-CMV promoter in the absence of the tetracycline analog doxycycline (Dox). This promoter system has been shown to be highly effective for conditional expression of protein-coding cDNAs both in vitro and in vivo. Thus when adapted for use in the subject invention, shRNA expression can mediate target gene knockdown in the absence of Dox both in vitro and in vivo.

Figure 3:
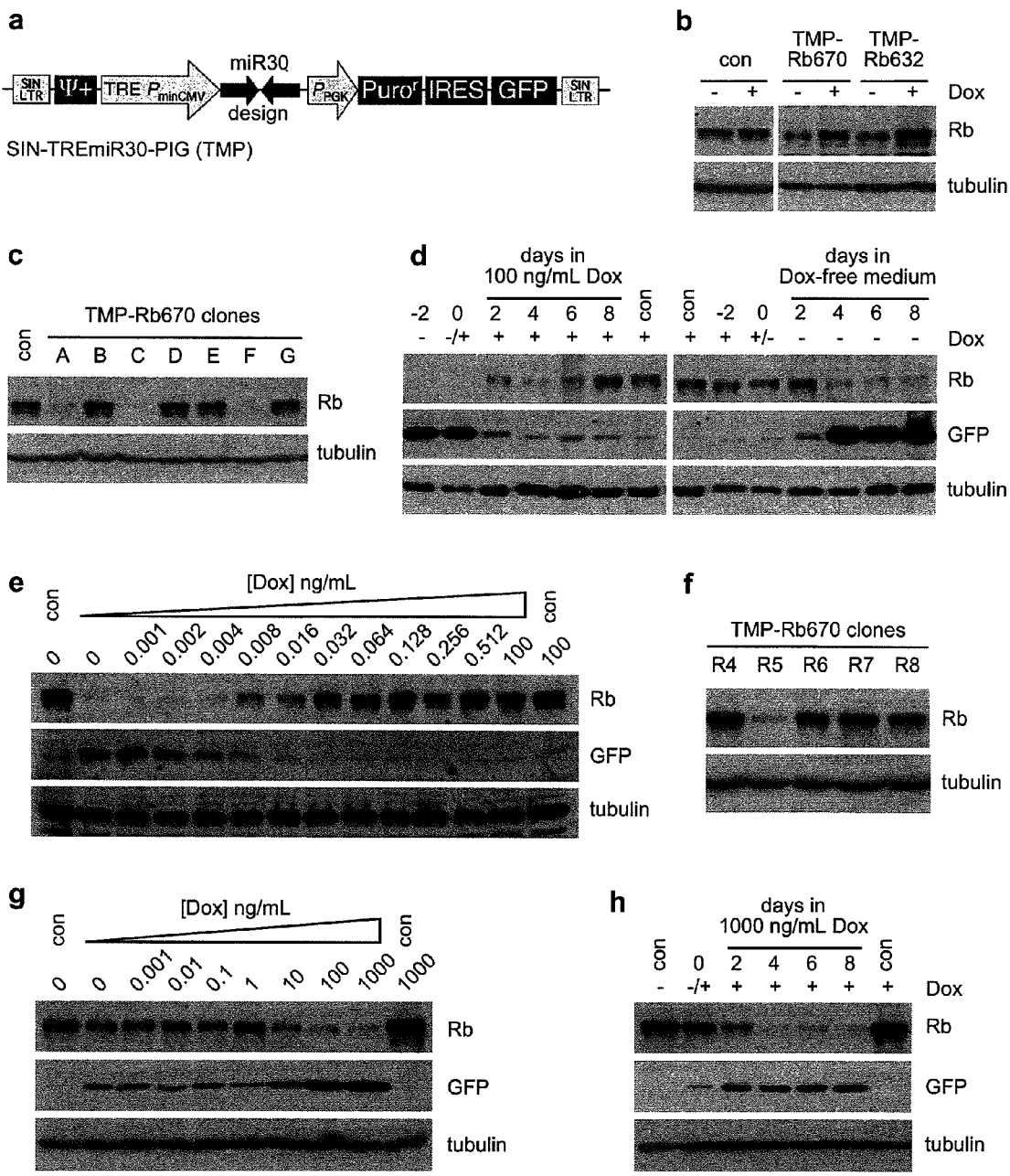
FIG. 3 shows stable and regulatable shRNA expression from a tet-responsive RNA polymerase II promoter. (A) Provirus layout of the SIN-TREmiR30-PIG (TMP) retroviral vector. (B) Western blot analysis of Rb expression in HeLa-tTA cells infected with TMP-Rb.670. Cells were treated with 100 ng/mL Dox for 4 days prior to harvesting. Control uninfected HeLa-tTA cells treated with Dox are also shown. (C) Rb expression in homogeneous cultures derived from single-cell clones of HeLa-tTA cells infected at single copy with TMP-Rb.670. Cells were cultured in normal, Dox-free medium prior to harvesting. con=control uninfected HeLa-tTA cells. (D) Dox dose/response analysis of Rb expression in HeLa-tTA clone Rb.670C. Cells were cultured for 8 days in the indicated Dox concentration prior to harvesting. Control uninfected HeLa-tTA cells (con) cultured with or without Dox are also shown. Note the presence of a non-specific band in the GFP immunoblot, running just below GFP. (E) Rb expression in HeLa-tTA clone Rb.670C cells over time in response to shifting into or out of Dox. Cells were cultured without Dox (left panels) or in 100 ng/mL Dox (right panels) for eight days prior to shifting them into 100 ng/mL Dox or Dox-free medium, respectively. Again, note the presence of a faint non-specific band in the GFP immunoblot. Similar results were observed for all Rb.670 clones showing good Rb knockdown in Dox-free medium (C, above), with some clonal variation in kinetics. In addition, similar results were obtained using other mishRNAs targeting Rb and PTEN (data not shown). (F) Rb expression in homogeneous cultures derived from single-cell clones of U2OS-rtTA cells infected at around 1% efficiency with TMP-Rb.670. Cells were cultured in 1000 ng/mL Dox for several days prior to harvesting. (G) Dox dose/response analysis of Rb expression in U2OS-rtTA clone Rb.670R5 cells. Cells were cultured for 8 days in the indicated Dox concentration prior to harvesting. Control uninfected U2OS-rtTA cells cultured with or without Dox are also shown. (H) Rb expression in U2OS-rtTA clone Rb.670R5 cells in response to Dox treatment. Cells were cultured without Dox for eight days prior to shifting them into 1000 ng/mL Dox. Note that Rb.670R5 cells express some GFP in Dox-free medium, and Rb levels are slightly decreased compared with controls, indicating slightly leaky expression from the TRE-CMV promoter in this particular clone.

Using a SIN vector backbone, Applicants cloned a mishRNA targeting human Rb (Rb.670) downstream of the TRE-CMV promoter, producing SIN-TREmiR30-PIG, or TMP-Rb.670; FIG. 3A). HeLa cells stably expressing the tet transactivator protein tTA (tet-off) were infected with TMP-Rb.670 at single copy in the absence of Dox. Rb levels in these cell populations were slightly decreased compared with uninfected controls, indicating potential shRNA production from the TRE-CMV promoter (FIG. 3B). Indeed, when single cell clones were generated from this population, 6 of 13 showed excellent Rb knockdown (FIG. 3C and data not shown), dem onstrating that the TRE-CMV promoter can effectively drive shRNA expression at low copy number.

To examine inducible regulation of shRNA expression, Rb.670C cells, which showed significant Rb knockdown in Dox-free medium (FIG. 3C), were cultured in various Dox concentrations for many days. Cell growth and viability were indistinguishable at all Dox concentrations. However, Applicants observed a clear dose-dependency of Rb expression, with maximum Rb knockdown achieved in low Dox concentrations and vice versa (FIG. 3D). At Dox concentrations of less than 0.005 ng/mL, Dox produced minimal Rb expression. However, cells grown in 0.008 ng/mL Dox showed slight de-repression of Rb. Normal Rb expression was restored in cells cultured in approximately 0.05 ng/mL Dox and higher, suggesting that shRNA expression is not leaky at these Dox concentrations.

Thus, Dox concentration can tightly control the extent of stable gene knockdown. This effect was also observed in time-course studies, where Applicants observed normalization of Rb expression upon Dox addition, and rapid Rb knockdown upon Dox removal (FIG. 3E), demonstrating the reversibility of the induced mishRNA expression. Remarkably, in all cases GFP and Rb levels were inversely correlated (FIGS. 3D and 3E), with intermediate GFP expression observed between 0.002 and 0.008 ng/mL Dox. As GFP and shRNA are produced from the same transcript, GFP expression may be regarded as a surrogate marker of shRNA production.

A great advantage of tet-regulated systems is that expression from the TRE-CMV promoter can be either induced (tet-ON) or repressed (tet-OFF) by Dox, depending on which tet transactivator protein is used. To test a tet-ON shRNA expression system, Applicants utilized U2OS cells stably expressing the reverse tTA (rtTA) protein, which in contrast to tTA, requires Dox to activate transcription.

Applicants also isolated a clone (Rb.670R5; FIG. 3F) of U2OS cells infected with TMP-Rb.670 and stably expressing the reverse tTA (rtTA; tet-on) protein. As predicted, Dox concentration and Rb knockdown were positively correlated in these cells (FIGS. 3G and 3H).

At Dox concentrations of less than 0.005 ng/mL, Dox produced minimal Rb expression. However, cells grown in 0.008 ng/mL Dox showed slight de-repression of Rb. Normal Rb expression was restored in cells cultured in approximately 0.05 ng/mL Dox and higher, suggesting that shRNA expression is not leaky at these Dox concentrations. As GFP protein is translated from an IRES, it can be produced from transcripts originating from both the PGK and TRE-CMV promoters. As GFP is not detected in cells grown in high Dox concentrations, it appears that GFP production from the PGK promoter transcript is very weak. Our results suggest that the majority of GFP in untreated Rb.670C cells arises from the CMV-TRE transcript, production of which is blocked by Dox in a dose-dependent manner. As the TRE-CMV transcript also carries the miR30-based shRNA fold, GFP expression may be regarded as a surrogate marker of shRNA production.

Using the same Tet-responsive system, good protein expression regulation was also achieved in several other cell clones, including those expressing a PTEN-miR30 construct.

These observation verifies that low copy delivery of the TMP vector (also lacking a Pol III promoter) allows regulated mishRNA expression in either tet-on or tet-off configurations, and altering Dox concentration in this system allows tight control of the extent of stable gene knockdown.

Example VII

Reversible Induction of Pol II-Driven Tet-Responsive p53 shRNA Production in Primary Cells The instant regulatable shRNA expression is not only operable in immortalized cell lines, but also functional to regulate suppression of genes (e.g., the tumor suppressor gene p53) in primary cells.

For example, inactivation of the tumor suppressor p53 immortalizes wild type MEFs, and transforms MEFs overexpressing oncogenic Ras. Early passage MEFs were co-transduced with TMP-p53.1224 and a retrovirus expressing the tTA (tet-off) protein. Many doubly infected MEFs (designated wild type/tTA/TMP-p53.1224, or WtT) showed stable p53 knockdown when cultured in Dox-free medium. WtT cells plated at low density formed colonies comparable in size and number to those formed by p53-null MEFs (FIG. 4A), suggesting that p53 was functionally inactivated in most cells. Colony formation of WtT cells cultured in Dox in parallel was similar to that of control cells (FIG. 4A), suggesting normal p53 expression. p53-null MEF growth was unaffected by Dox, ruling out non-specific effects (FIG. 4A).

Figure 4:
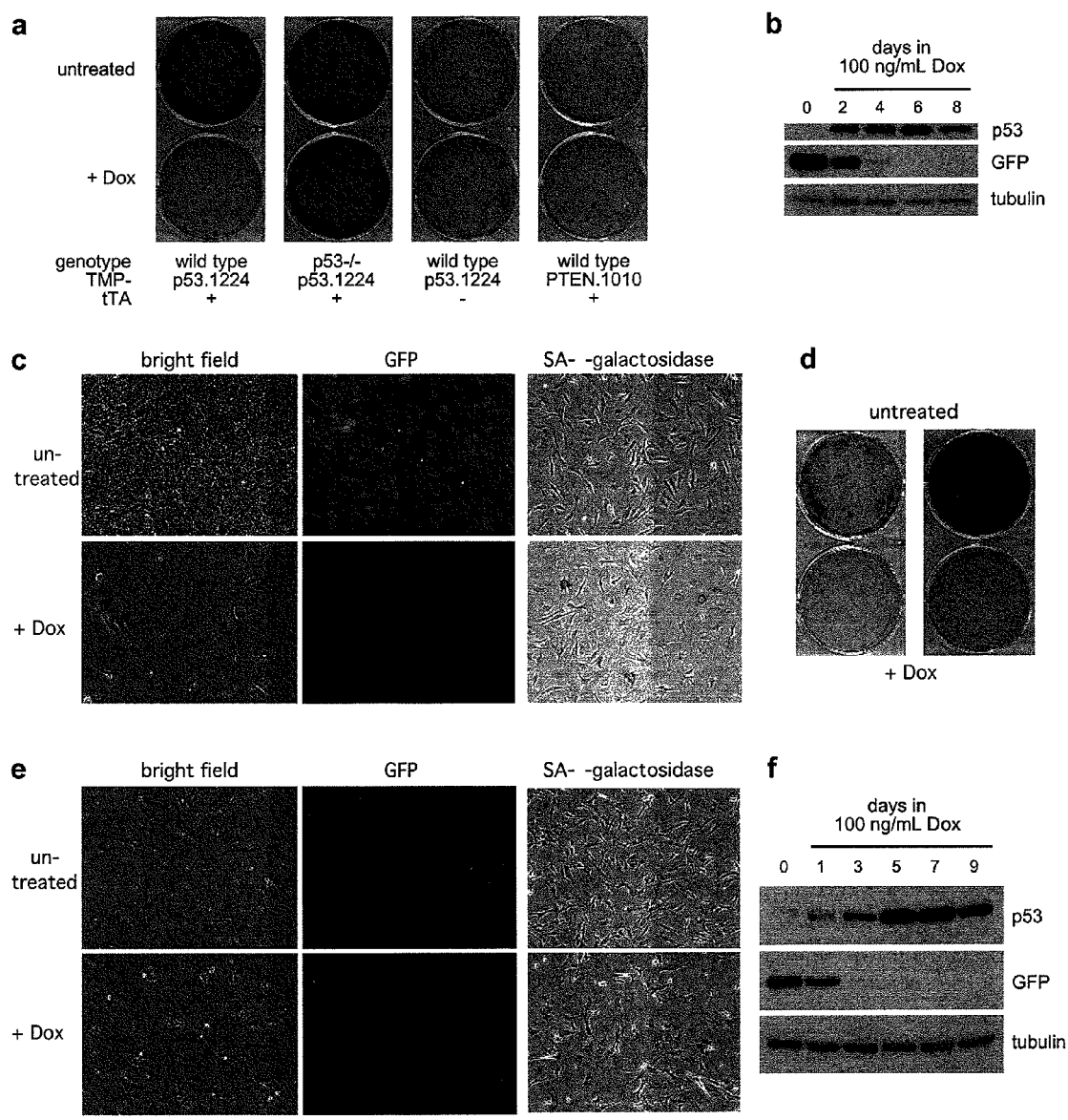
FIG. 4 shows reversible p53 knockdown in primary MEFs. (A) Colony formation assays of wild type MEFs doubly infected with TMP-p53.1224 and tTA. Cells were seeded in 6 well plates at 5000 cells/well, and grown for 8 days before harvesting. Upper wells contained Dox-free medium, whereas lower wells contained 100 ng/mL Dox. Positive control p53-null MEFs are shown, as are negative control wild type MEFs infected with TMP-p53.1224 alone or with IMP-PTEN.1010 plus tTA. (B) Western blot analysis of p53 and GFP expression in cells expanded from a single-cell clone of wild type MEFs infected with TMP-p53.1224 and tTA (WtT cells). Cells were cultured in 100 ng/mL Dox for various times prior to harvesting. (C) Morphology and GFP fluorescence of WtT cells originally plated at colony formation density, and cultured in Dox-free medium (upper panels) or 100 ng/mL Dox (lower panels). Right panel: SA-β-gal staining of WtT cells cultured in Dox-free medium (upper) or 100 ng/mL Dox (lower). (D) Left panel: Colony formation assay for WtT cells cultured for 8 days in 100 ng/mL Dox, then seeded in Dox free medium (upper well) or 100 ng/mL Dox (lower well). Right panel: Colony formation assay of cells equivalent to those in the upper well of the left panel (formerly Dox-treated, claimant WtT cells after extended culture in Dox-free medium). Cells were seeded and harvested as in (A). (E) Morphology, GFP fluorescence, and SA-β-gal staining of WtT cells infected with Ras and cultured in normal medium (upper panels) or 100 ng/mL Dox (lower panels). (F) Western blot analysis of p53 and GFP expression in WtT cells infected with Ras. Cells were cultured in 100 ng/mL Dox for various times prior to harvesting.

Applicants also isolated several WtT clones and examined their p53 regulation in response to Dox. p53 expression in WtT cells increased rapidly and GFP expression was lost upon Dox treatment (FIGS. 4B and 4C). WtT clones cultured in Dox failed to form colonies when plated at low density. Instead, by day 8 of Dox treatment, all cells had a flattened morphology characteristic of senescent cells, and many were positive for senescence-associated β-alactosidase (SA-β-gal; FIG. 4C). This dormant phenotype was stable for weeks of continuous culture in Dox. Therefore, p53.1224 shRNA expression can be tightly regulated by Dox treatment in wild type MEFs doubly infected with tTA and TMP-p53.1224.

The rapid and coordinated senescence response observed when endogenous p53 expression was restored in MEFs immortalized by p53 knockdown was reversed upon Dox removal (FIG. 4D, left panel, upper well), in agreement with previous observations in other MEF culture systems. Control cells continually cultured in Dox remained dormant (FIG. 4D, left panel, lower well). Newly proliferating cells (FIG. 4D, left panel, upper well) remained responsive to p53 re-expression, as they lost GFP expression and failed to form colonies when re-plated in Dox (FIG. 4D, right panel, lower well).

These results suggest that wild type MEFs can be reversibly switched between cycling and senescent states simply by regulating p53 knockdown. WtT cells transformed by infection with activated Ras (FIG. 4E, upper panels) also became morphologically senescent and SA-β-gal positive when treated with Dox (FIG. 4E, lower panels), with p53 and GFP expression changes similar to that of parental WtT cells (FIG. 4F).

Furthermore, Applicants conclude that restoration of p53 expression in wild type MEFs immortalized by stable p53 knockdown causes a rapid and coordinated senescence response. This demonstrates that at least in cancers with p53 loss-of-function mutations, cancers can be treated by restoring p53 expression to induce senescence. This technique can also be extended to test any potential target genes whose functions are lost in diseases, such as in cancer. Specifically, the system of the instant invention may be used to test whether loss-of-function of a candidate gene causes certain disease state, and whether restoring such target gene function in diseased tissues can reverse the disease status, or at least slow down disease progression.

Example VIII

Reversible in vivo Gene Knockdown Using Tet-Responsive Promoter

Figure 5:
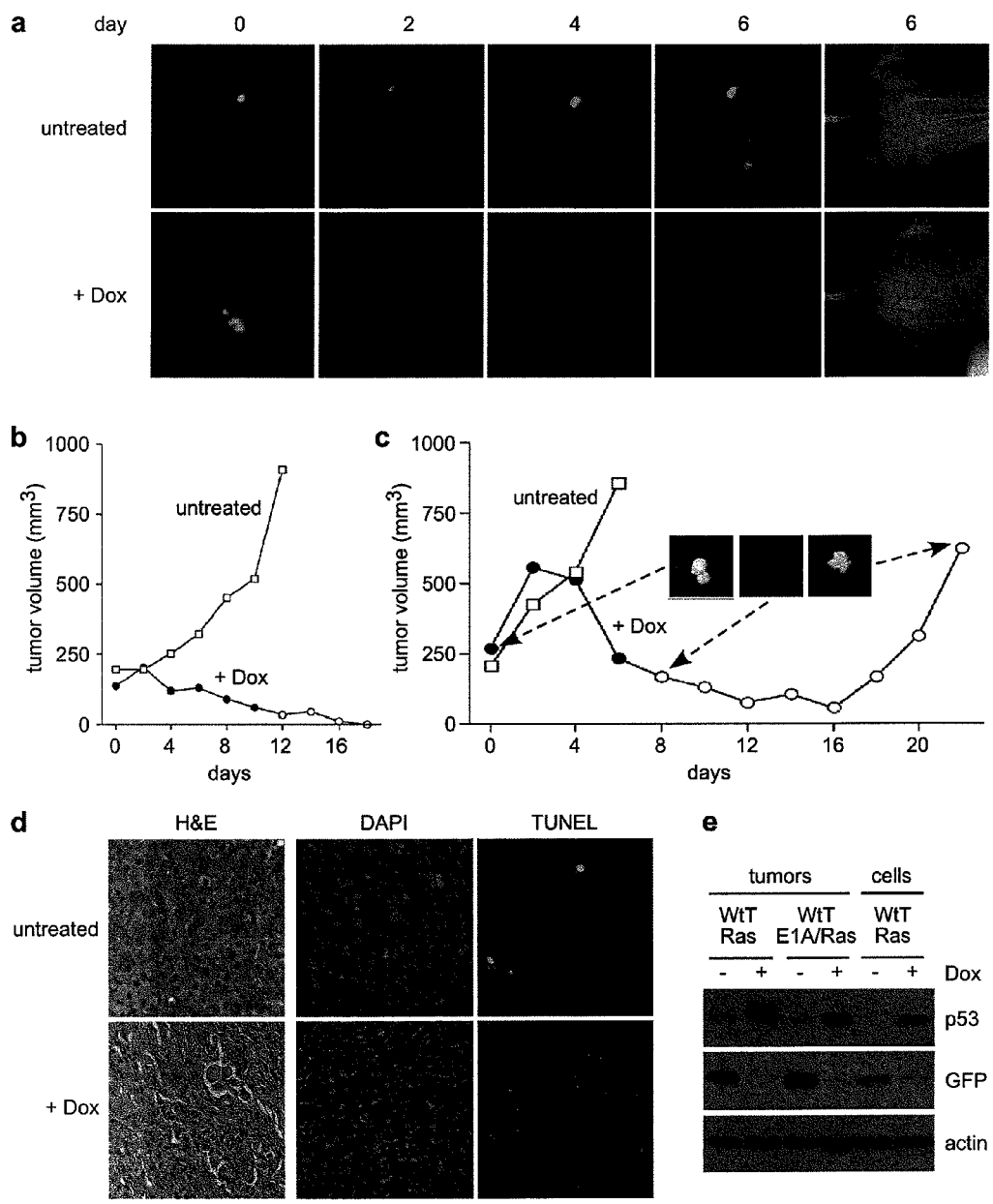
FIG. 5 shows regulated p53 knockdown in tumors. (A) GFP and standard imaging of representative tumor-bearing nude mice, with Dox treatment commencing at day 0 (lower panels). Untreated controls are shown (upper panels). (B) Representative tumor growth curves for WtT-Ras tumors in an untreated mouse (open squares), or a mouse treated for 10 days with Dox (filled circles indicate Dox treatment) commencing at day 0. Each data point is the average volume of 2 tumors for a single mouse. Similar results were obtained for 8 different WtT-Ras clones, with slightly differing kinetics. (C) Representative tumor growth curves for WtT-EIA/Ras tumors in an untreated mouse (open squares), or a mouse treated for 7 days with Dox (filled circles indicate Dox treatment) commencing at day 0. Each data point is the average volume of 2 tumors for a single mouse. Insets show GFP status of a single tumor at various times. (D) Histological analysis of cell morphology and apoptosis in representative nude mouse tumors harvested from untreated mice or mice treated with Dox for several days. (E) Western blot analysis of p53 and GFP expression in representative WtT-Ras and WtT-E1A/Ras tumors harvested from untreated mice or mice treated with Dox for several days. Cultured WtT-Ras cells treated with Dox are shown as a control.

Tet-regulated over-expression systems have revolutionized the study of the role of oncogenes in tumor survival in vivo. Tet-regulated RNAi holds similar promise for regulated knockdown of tumor suppressor genes. To illustrate this concept, Applicants injected WtT-Ras MEFs subcutaneously into the flanks of nude mice formed visible, rapidly growing and strongly GFP positive tumors after approximately 2 weeks, verifying that these cells were functionally transformed (FIG. 5A; upper panels). To inactivate p53.1224 shRNA in established tumors, mice were treated with Dox via their drinking water. After only 2 days of Dox treatment, tumor GFP intensity was markedly diminished compared with untreated mice, and after 4 days tumors were almost GFP negative (FIG. 5A). Remarkably, tumor growth slowed upon Dox treatment, and tumors began shrinking after approximately 4 to 6 days (FIG. 5B). Animals treated with Dox for 10 days often showed continued tumor regression and became tumor-free (FIG. 5B). This regression was p53-dependent, as tumors derived from p53-null MEFs infected with tTA, TMP-53.1224 and Ras lost GFP expression but continued to grow when treated with Dox (data not shown). Similar results were obtained for several WtT-Ras clones and WtT clones infected with E1A/Ras, with variable tumor growth rates and regression kinetics (data not shown).

Dox-treated animals with regressing tumors were taken off Dox treatment after various times. In many cases, usually when initial tumor size was less, mice became tumor-free and remained so for weeks. However, removing Dox from animals with larger regressing tumors or after a briefer Dox treatment often allowed renewed GFP expression and tumor growth (FIG. 5C). Interestingly, tumors isolated from Dox-treated animals contained cells with unusually compact nuclei, and widespread apoptosis was seen compared with untreated controls (FIG. 5D), suggesting that tumor regression was at least in part due to p53-dependent apoptosis. Indeed, as predicted, p53 expression was dramatically elevated in tumors from Dox-treated animals (FIG. 5E).

In summary, by adapting a standard Pol II promoter-driven tet-responsive promoter normally used for inducible protein expression, Applicants for the first time have demonstrated inducible and reversible target gene knockdown in vivo. p53 re-expression in tumors caused regression associated with widespread apoptosis, in contrast to the senescence observed when p53 was re-expressed in the same cells in culture. These findings highlight the ability of this technology for the study of many aspects of biology, including identification and/or validation of potential drug targets in animal models. The tet system has obvious advantages over unidirectional Cre-lox strategies, and many key reagents, such as tissue-specific tet transactivator mice, are readily available.

In summary, expression of miRNA-design short hairpin RNAs (shRNAs) allows stable, post-transcriptional suppression of gene activity, which is optionally reversible. Applicants have developed a new retroviral vector system that uses RNA polymerase II promoters to express shRNAs based on the human miR30 precursor. Single copy expression of shRNAs from this vector yields potent and stable gene knockdown in cultured cells and in vivo. Expression of an shRNA targeting p53 using this system mimics complete p53 loss and renders tumor cells chemoresistant in vivo. By improving standard tet-inducible promoters for shRNA expression, we show stable, incremental, and reversible gene knockdown of various target genes in tet-on or tet-off configurations. Interestingly, cultured wild type mouse fibroblasts can be switched from proliferative to senescent states simply through regulated knockdown of p53. We find that tumors derived from wild type mouse fibroblasts transformed by Ras overexpression and p53 knockdown regress upon p53 re-activation in vivo, suggesting that ongoing suppression of p53 is essential for tumor maintenance in this context. This system proves useful for studying potential therapeutic targets in cancer, and in most other biological systems.

All vectors described in these experiments are compatible with genome-wide, sequence verified banks of miR30 shRNAs (or any other similar banks of miR shRNAs) targeting human and mouse genes, creating a formidable resource for diverse, large scale RNAi studies in mammalian systems.

Methods

The following methods and reagents were used in the Examples above. These are merely for illustrative purpose, and are by no means limiting. Other comparable minor variations can be readily made without undue experimentation for adapting to specific problems.

Vector Construction.

The retroviral vector MSCV-PIG has an EcoRI site in the polylinker and another between the Puro$^R$ cassette and the IRES sequence. To facilitate cloning into the polylinker, the second site was destroyed using a PCR-based strategy: a PCR product was generated using MSCV-PIG template, forward primer 5'-TCTAGGCGCCGGAATTAGATCTCTCG-3' (SEQ ID NO: 1), and reverse primer 5'-CCTGCAATTGGATGCATGGGGTCGTGC-3' (SEQ ID NO: 2), and digested with BglII and MfeI. This fragment was cloned into MSCV-PIG digested with BglII/EcoRI, yielding MSCV-PIGdRI. MSCV-U6miR30-PIG was made by ligating the 762 bp BamHI-MfeI "U6-miR30 context" cassette from pSM2 into MSCV-PIGdRI digested with BglII/EcoRI. MSCV-LTRmiR30-PIG was made by ligating the 256 bp SalI-MfeI "miR30 context" cassette from pSM2 into MSCV-PIGdRI digested with XhoI/EcoRI. MSCV-LTRmiR30-SV40GFP (LMS) was made in two steps. Firstly, a ~1.2 kb EcoRI-ClaI SV40GFP fragment from pBabeGFP was ligated into MSCV-puro (Clontech) digested with EcoRI/ClaI, forming MSCV-SV40GFP. This was digested with XhoI/EcoRI, and the 256 bp SalI-MfeI "miR30 context" cassette from pSM2 was inserted, forming MSCV-LTRmiR30-SV40GFP. SIN-PIGdRI was made by ligating the 2524 bp EcoRI-SaiI fragment from MSCV-PIGdRI into pQCXIX (Clontech) digested with EcoRI/XhoI. SIN-TREmiR30-PIG was constructed in two steps. Firstly, a PCR product spanning the TRE-CMV promoter was generated using template plasmid pQTXIX (a kind gift from Abba Malina, generated by cloning the XbaI-EcoRI TRE-CMV promoter fragment from pUHD10.3 into pQCXIX (Clontech) digested with XbaI/EcoRI), using the primers 5'-GAATTGAAGATCT GGGGGATCGATC-3' (SEQ ID NO: 3) and 5'-CATCAATTGCTAGAATTCTGGTTGCT CGAGAGGCTGGATCGGTCCCGGTGTCTTC-3' (SEQ ID NO:4). This PCR product was digested with BglII/MfeI and ligated into SIN-PIGdRI digested with BglII/EcoRI (removing its CMV promoter), forming SIN-TRE-PIG. SIN-TREmiR30-PIG was completed by ligating the 256 bp SalI-MfeI "miR30 context" cassette from pSM2 into SIN-TRE-PIG digested with XhoI/EcoRI. DNA fragments encoding various mishRNA folds were generated using oligonucleotide template PCR as described previously, or subcloned as 110 bp XhoI/EcoRI fragments from the pSM2 mishRNA library. Oligonucleotides were designed at katandin.cshl.org: 9331/siRNA/RNAi.cgi?type=shRNA (incorporated herein by reference). PCR products were digested with XhoI/EcoRI and ligated into the unique XhoI/EcoRI sites within the "miR30 context" in the vectors described above.

Cell Culture and Expression Analysis

Cells were grown in DMEM containing 10% fetal bovine serum at 37° C. with 7.5% $CO_2$. Doxycycline (Clontech) was dissolved in water and generally used at a final concentration of 100 ng/mL. Medium containing Dox was refreshed every two days. Infections and colony formation assays were carried out as previously described. SA-β-gal activity was detected as previously described, with sample equilibration and X-gal staining done at pH 5.5. For western blotting analysis, Laemmli buffer protein lysates were run on SDS-PAGE, and transferred to Immobilon PVDF membrane (Millipore). Antibodies were anti-p53 (1:1000 IMX25, Vector Laboratories), anti-PTEN (1:1000 486, a kind gift from Michael Myers), anti-GFP (1:5000, Clontech), anti-tubulin (1:5000 B-5-1-2, Sigma), anti-actin (1:5000, Sigma), and anti-Rb (1:1000 G3-245, Pharmingen with 1:100 XZ-55 and C36 hybridoma supernatants).

Lymphoma Studies

Eμ-myc lymphomagenesis and drug treatment studies were performed as previously described (Schmitt, 2000; Hemann, 2003). Chemosensitive lymphoma cells were isolated from tumors arising in mice transplanted with Eμ-myc; $p19^{ARF}$+/− HSCs, which invariably lose the wild type $p19^{ARF}$ allele while retaining wild type p53.

Nude Mouse Studies

Approximately $10^6$ transformed cells were injected subcutaneously into the two rear flanks of nude mice. Mice were treated with 0.2 mg/mL Dox in a 0.5% sucrose solution in light-proof bottles, refreshed every four days. Tumor volume ($mm^3$) was calculated as (length×width$^2$×π/6). For analysis of protein expression, tumors were snap-frozen and pulverised in liquid nitrogen using a mortar and pestle. Powdered tumor was lysed in Laemmli buffer and western analysis was performed as above. For histology, tumor tissue was fixed for 24 hours in 4% formaldehyde in PBS prior to embedding and sectioning. Apoptosis was measured by TUNEL assay (In situ Cell Death Detection Kit, POD; Roche).

Results described herein above are published in *Nat. Genet.* 37(11): 1289-95, 2005 (Dickins et al., 2005). Other related work is published in *Nat. Genet.* 37(11): 1281-88, 2005 (Silva et al., 2005). The entire contents of these publications, including the related online (supplemental) information and contents of the publications cited therein are incorporated herein by reference. The subject system can also be used in lentiviral, pre-miR-30based siRNA expression vectors, such as those including a tetracyclin-responsive Pol II promoter and thus can be used to tightly regulate the expression of target genes in transduced cells. See Stegmeier et al., *Proc. Natl. Acad. Sci. U.S.A.* 102: 13212-17, 2005 (incorporated herein in its entirety).

Example IX

In Vivo Transgenic Animal Model for Tissue-Specific and Inducible Target Gene Knockdown This example demonstrates knockdown of a target gene, e.g., p53, in a tissue-specific, inducible and/or reversible manner, in a germline (transgenic) animal model.

To achieve regulated transgene expression in germline transgenic mice, two lines of transgenic mice were generated: one expressing a tet transactivator protein (either tTA/tet-off or rtTA/tet-on), optionally in a tissue-specific manner using tissue-specific promoters; and another harboring a tetracycline-responsive (TRE) promoter driving the transgene of interest. Crossing these two lines yielded double transgenic mice that expressed the transgene, in a Dox-regulatable manner (either tet-on or tet-off), in cells where the transactivator (tTA or rtTA) was expressed.

Alternatively, the tTA or rtTA construct may be introduced (e.g. via infection or transfection, etc.) into cells of a transgenic animal bearing TRE-mishRNA-expression cassette.

For example, to demonstrate that tet-regulated miR30-based shRNA expression can be achieved in animals, Applicants generated several transgenic founder lines harboring a TRE-p53.1224 shRNA cassette (using standard pronuclear injection protocols). To test shRNA activity in these animals, Applicants isolated MEFs (mouse embryonic fibroblasts) from F2 transgenic embryos and wild-type controls, infected them with a retrovirus expressing the tTA (tet-off) protein, and assessed p53 knockdown after p53 induction by adriamycin. Specifically, primary MEFs derived from embryos from a cross between wild-type B6 females mated to TRE-p53.1224 founder lines A and B, were infected with either tTA-IRES-Neo or tTA-IRES-GFP retrovirus. Then tTA-IRES-Neo MEFs were selected for 7 days in G418 prior to harvesting in order to eliminate uninfected cells. The tTA-IRES-GFP MEFs were unselected, though the MEFs were infected at high percentage. All cells were adriamycin treated prior to harvesting.

Of the two founder lines tested so far, one (line A) showed striking p53 knockdown in transgene-positive cells (results not shown). This knockdown was similar to that seen when the p53.1224 shRNA was expressed from a retroviral LTR promoter (supra; Dickins et al., *Nat. Genet.* 37(11): 1289-95, 2005). Importantly, p53 induction was normal in uninfected transgene-positive cells (e.g., by comparing founder line A MEFs either uninfected or infected with tTA-IRES-Neo. All cells were adriamycin treated prior to harvesting. Results not shown). This demonstrates that shRNA expression and p53 knockdown is tTA-dependent and not leaky.

Moreover, as expected, these MEF lines showed a rapid re-expression of p53 upon Doxycycline treatment, indicating that shRNA expression was tightly controlled by Doxycycline (results not shown).

To our knowledge, the above experiments for the first time demonstrated that tetracycline effectively regulated shRNA expression in a germline transgenic setting. This enables one to reversibly switch any endogenous gene on or off, simply by administering a reversible activator or inhibitor of a transcriptional regulator, such as Doxycycline (or other Tet homolog), preferably via drinking water. This technology is especially powerful in examining gene function in vivo, for example, during embryonic or postnatal development, tumorigenesis, or after treatment of tumors with chemotherapeutic drugs.

As indicated above, Applicants have also crossed the TRE-p53.1224 transgenic mice to established transgenic lines that express the tTA (tet-off) protein in a tissue-specific manner. As expected, Applicants detected p53.1224 siRNA in the liver of LAP-tTA; TRE-p53.1224 double trangenic mice, where tTA expression was restricted to the liver (lane 2 of FIG. 6). After 4 days of doxycycline administration, some attenuation of siRNA production was observed (lane 3 of FIG. 6). Applicants have also been assessing p53 knockdown in the liver of these mice, in order to determine whether longer term doxycycline administration will further or completely block siRNA production. Note that the spleens of these mice were devoid of siRNA (see lanes 4-6 of FIG. 6), consistent with liver-specific expression of the siRNA.

The system can also be used to generate animal models for studying the effect of turning on/off certain target genes in the progression of certain diseases, such as cancer.

For example, the Eµ-myc mouse is prone to developing lymphoma, which is accelerated further by loss of p53 function. To model this process using tet-regulated p53 knockdown in vivo, Applicants crossed Eµ-myc mice to TRE-p53.1224 mice and Eµ-tTA mice, which expressed tTA specifically in the B cell compartment. As myc and tTA should be expressed coordinately in B cells of the Eµ-myc; Eµ-tTA; TRE-p53.1224 triple transgenic mice, Applicants expected reversible p53 knockdown in oncogene-expressing cells.

Figure 6:
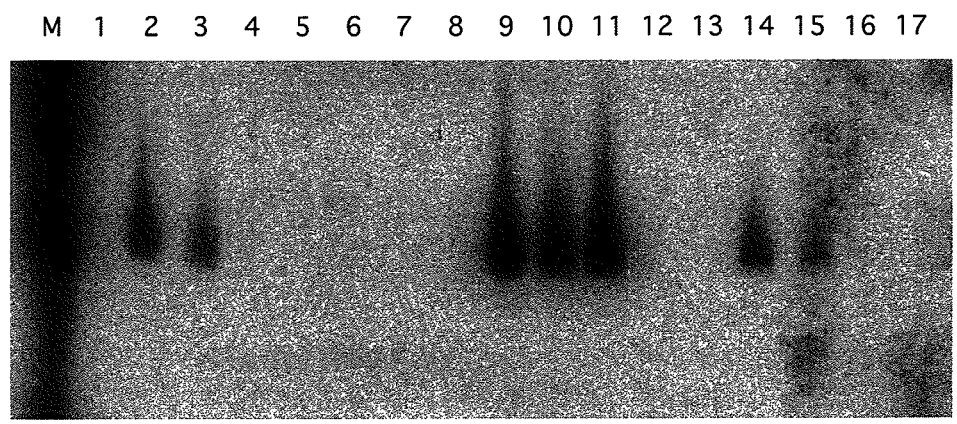
FIG. 6 shows an siRNA northern blot of tissues isolated from animals of various genotypes, probed with a labelled oligonucleotide that hybridizes to the p53.1224 siRNA. The individual lanes are: M: Molecular weight marker; 1: LAP-tTA liver; 2: LAP-tTA;TRE-1224 liver; 3: LAP-tTA;TRE-1224 liver after 4 days Doxycycline administration; 4: LAP-tTA spleen; 5: LAP-tTA;TRE-1224 spleen; 6: LAP-tTA;TRE-1224 spleen after 4 days Doxycycline administration; 7: Eu-myc;TRE-1224 mouse 4-1 spleen; 8: Eu-myc;TRE-1224 mouse 6-4 spleen; 9: Eu-myc;Eu-tTA;TRE-1224 mouse #1 spleen; 10: Eu-myc;Eu-tTA;TRE-1224 mouse #2 spleen; 11: Eu-myc;Eu-tTA;TRE-1224 mouse #1-2 spleen; 12 & 13: Spleen (12) and lymph node (13) from a tumor-bearing nude mouse recipient of Eu-myc lymphoma cells; 14 & 15: Spleen (14) and lymph node (15) from a tumor-bearing nude mouse recipient of Eu-myc;Eu-tTA;TRE-1224 lymphoma cells; 16 & 17: Spleen (16) and lymph node (17) from a tumor-bearing nude mouse recipient of Eu-myc;Eu-tTA;TRE-1224 lymphoma cells, after 14 days Doxycycline administration.

Consistent with this prediction, in a spleen (a tissue enriched for lymphoma cells) isolated from lymphoma-laden triple transgenic mice, Applicants observed highly abundant p53.1224 siRNA, at levels known to promote p53 knockdown and tumor progression (lanes 9-11 of FIG. 6). In contrast, spleens from Eµ-myc; TRE-1224 double transgenic mice do not express the siRNA, indicating that the TRE-1224 transgene requires tTA for expression.

Lymphoma cells isolated from these triple trangenic mice were then transplanted into several recipient nude mice to allow controlled p53 re-activation. Specifically, tumor-bearing recipient mice were treated with Doxycycline. Survival of heavily tumor-bearing transplant recipients was extended by many days when doxycycline was administered via the drinking water. Furthermore, p53.1224 siRNA expression was completely suppressed in the lymph nodes and spleen of these treated mice, indicating effective switching of shRNA expression in vivo.

These results demonstrated that Applicants can produce transgenic mice where miR30-based shRNA production was tissue-specific, and can be inducibly and reversibly regulated simply by administering or omitting doxycycline in the drinking water.

The practice of aspects of the present invention may employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I-IV (D. M. Weir and C. C. Blackwell, eds., 1986); *Manipulating the Mouse Embryo,* (Cold Spring Harbor Laboratory Press, Cold Spring Harbor, N.Y., 1986). All patents, patent applications and references cited herein are incorporated in their entirety by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A non-human mammal comprising a population of cells, wherein each cell in said population harbors only a single, stably integrated copy of a nucleic acid construct for expression of a synthetic miR30-based shRNA, wherein said construct contains only a single tetracycline responsive RNA Polymerase II (Pol II) promoter operably linked to a sequence encoding only a single synthetic mir30-based shRNA directed against a target gene, wherein in said population of cells, induced expression of the synthetic miR30-based shRNA is sufficient to inhibit expression of the target gene by at least about 80%.

2. The non-human mammal of claim 1, wherein the promoter comprises a tet-off promoter, such that the synthetic miR30-based shRNA is expressed in the absence of tetracycline or a tetracycline analog.

3. The non-human mammal of claim 1, wherein the promoter comprises a tet-on promoter such that the synthetic miR30-based shRNA is expressed when the mammal is treated with tetracycline or a tetracycline analog.

4. The non-human mammal of claim 1, 2 or 3, wherein the population of cells further comprises an additional nucleic acid construct encoding tetracycline-controlled transactivator (tTA) or reverse tetracycline-controlled transactivator (rtTA).

5. The non-human mammal of claim 1, 2 or 3, wherein the population of cells further comprises an additional nucleic acid construct encoding Cre recombinase.

6. The non-human mammal of claim 1, 2 or 3, wherein the single tetracycline responsive RNA Polymerase II (Pol II) promoter is a LoxP-stop-LoxP system promoter.

7. The non-human mammal of claim 1, 2 or 3, which is a chimeric mammal, whose somatic or germ cells comprise said population of cells.

* * * * *